US010046067B2

(12) United States Patent
Yun et al.

(10) Patent No.: US 10,046,067 B2
(45) Date of Patent: *Aug. 14, 2018

(54) DECORIN GENE DELIVERY SYSTEM AND CANCER TREATMENT

(71) Applicant: GENEMEDICINE CO., LTD., Seoul (KR)

(72) Inventors: Chae-Ok Yun, Seoul (KR); Joo Hang Kim, Seoul (KR)

(73) Assignee: GENEMEDICINE CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/081,110

(22) Filed: Mar. 25, 2016

(65) Prior Publication Data

US 2017/0080106 A1   Mar. 23, 2017

Related U.S. Application Data

(63) Continuation of application No. 11/816,751, filed as application No. PCT/KR2006/000657 on Feb. 24, 2006, now Pat. No. 9,468,690.

(30) Foreign Application Priority Data

Feb. 25, 2005 (KR) .................. 10-2005-0015793

(51) Int. Cl.
*A61K 48/00* (2006.01)
*A61K 38/16* (2006.01)
*C07K 14/005* (2006.01)
*C07K 14/705* (2006.01)
*C12N 7/00* (2006.01)

(52) U.S. Cl.
CPC .......... *A61K 48/005* (2013.01); *A61K 38/162* (2013.01); *C07K 14/005* (2013.01); *C07K 14/70578* (2013.01); *C12N 7/00* (2013.01); *C12N 2710/10033* (2013.01); *C12N 2799/022* (2013.01)

(58) Field of Classification Search
None
See application file for complete search history.

(56) References Cited

U.S. PATENT DOCUMENTS

| | | | |
|---|---|---|---|
| 4,797,368 A | 1/1989 | Carter et al. | 435/320 |
| 5,139,941 A | 8/1992 | Muzyczka et al. | 435/172.3 |
| 5,601,818 A | 2/1997 | Freeman et al. | 424/93.21 |
| 5,631,236 A | 5/1997 | Woo et al. | 514/44 |
| 6,524,573 B1 | 2/2003 | Iozzo | 424/93.2 |
| 2003/0032591 A1 | 2/2003 | Ruoslahti et al. | 514/12 |
| 2004/0205832 A1 | 10/2004 | Meade et al. | 800/7 |

FOREIGN PATENT DOCUMENTS

| | | | | |
|---|---|---|---|---|
| WO | WO 94/02167 | 2/1994 | ............. | A61K 37/16 |
| WO | WO 96/30385 | 10/1996 | ............. | C07H 21/00 |
| WO | WO 2004/035616 | 4/2004 | ........... | C07K 14/005 |
| WO | WO 2004/076668 | 9/2004 | ............. | C12N 15/52 |

OTHER PUBLICATIONS

Decorin—Protein—NCBI downloaded Jun. 21, 2017; pp. 1-2.*
Bett An efficient and flexible system for construction of adenovirus vectors with insertions or deletions in early regions 1 and 3. Proc. Natl. Acad. Sci. USA vol. 91, pp. 8802-8806, Sep. 1994.*
Borisy et al., (2003). "Systematic discovery of multicomponent therapeutics". www.pnas.org/cgi.doi/10.1073/pnas.1337088100.
Eickelberg et al., (1999). "Extracellular matrix deposition by primary human lung fibroblasts in response to TGF-β1 and TGF-β3". *Am. J. Physiol. 276 (Lung Cell. Mol. Physiol.)*, 20:L814-L824.
Fischer et. al, (2000). "Local expression of bovine decorin by cell-mediated gene transfer reduces neointimal formation after balloon injury in rats". *Circ. Res. Journal of the American Heart Association* 86;676-683.
Fischer et al., (2001). "Retroviral overexpression of decorin differentially affects the response of arterial smooth muscle cells to growth factors". *Arterioscler. Thromb. Vasc. Biol. Journal of the American Heart Association* 21;777-784.
Järveläinen et al., (2004). "Overexpression of decorin by rat arterial smooth muscle cells enhancescontraction of type i collagen in vitro". *Arterioscler. Thromb. Vasc. Biol. Journal of the American Heart Association* 2004;24;67-72; originally published online Nov. 13, 2003.
Reed et al., (2005). "Decorin prevents metastatic spreading of breast cancer". *Oncogene.* 24:1104-1110.
International Search Report (ISR) dated Jun. 5, 2006 in PCT/KR2006/000657.

* cited by examiner

*Primary Examiner* — Maria G Leavitt
(74) *Attorney, Agent, or Firm* — Harness, Dickey & Pierce, P.L.C.

(57) ABSTRACT

The present invention relates to a novel gene delivery system and recombinant adenovirus comprising the decorin-encoding sequence to enhance transduction efficiency of transgenes, a pharmaceutical anti-tumor composition comprising the recombinant adenovirus, a pharmaceutical composition having improved tissue penetration potency and a pharmaceutical composition for treating a disease or disorder associated with accumulation of excess extracellular matrix.

9 Claims, 29 Drawing Sheets

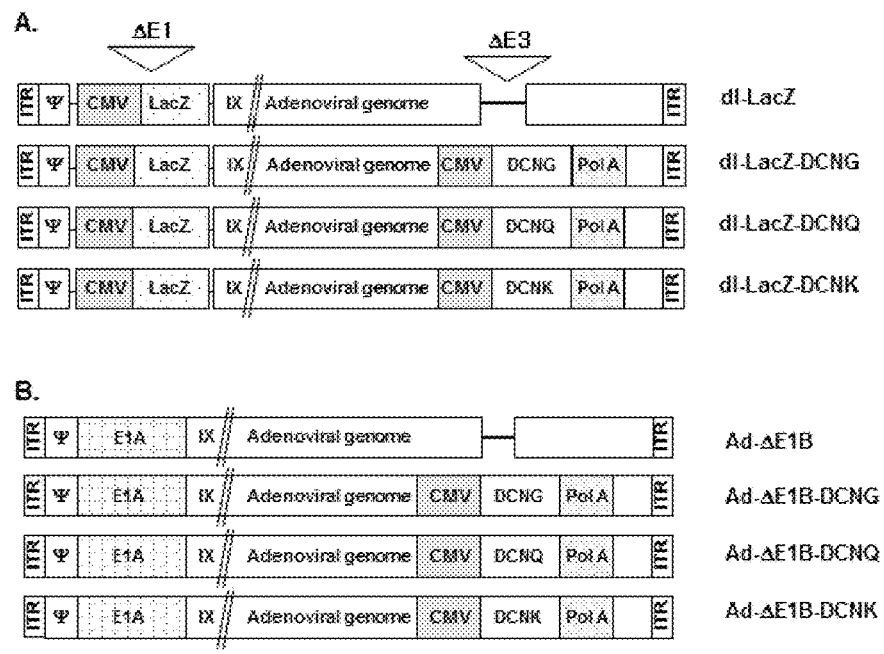
FIG. 1a
FIG. 1b

A. Cancer cells

B. Normal cells 1. dl-LacZ
2. Ad-ΔE1B
3. Ad-ΔE1B-DCNG
4. Ad-ΔE1B-DCNQ
5. Ad-ΔE1B-DCNK

DECORIN GENE DELIVERY SYSTEM AND CANCER TREATMENT

CROSS-REFERENCE TO RELATED APPLICATIONS

This application is a continuation of U.S. Ser. No. 11/816,751, now U.S. Pat. No. 9,468,690, filed 28 Aug. 2007 which claims priority to PCT Application No. PCT/KR2006/000657, filed on 24 Feb. 2006, which claims benefit of Korean Patent Application 10-2005-0015793, filed on 25 Feb. 2005. The entire disclosure of the applications identified in this paragraph is incorporated herein by references.

FIELD

The present invention relates to a novel gene delivery system and recombinant adenovirus, in particular, to a novel gene delivery system and recombinant adenovirus comprising a decorin-encoding sequence, a pharmaceutical anti-tumor composition comprising the recombinant adenovirus, a pharmaceutical composition characterized by improved tissue penetration potency and a pharmaceutical composition for treating a disease or disorder associated with accumulation of excess extracellular matrix.

BACKGROUND

Early adenovirus-based gene therapy usually employs replication-incompetent adenoviruses carrying a therapeutic gene with deleted E1 gene essential for adenovirus replication. However, these recombinant adenoviruses induce anti-tumor activity only in infected cells and a very small number of surrounding cells, exhibiting serious problems in clinical applications (Vile R G, Russell S J, Lemoine N R., *Gene Ther*, 2000, 7(1):2-8). To overcome such problems, the oncolytic adenovirus, ONYX-015(dl1520) selectively replicating in tumor cells was first developed by McCormick research group (Bischoff J R, et al., *Science*, 1996, 274 (5286):373-376; Heise C, et al., *Nat Med*, 1997, 3(6):639-645). The EIB 55 kDa gene-deleted adenovirus selectively replicates in tumor cells lacking functional p53. When the recombinant adenovirus infects normal cells, its proliferation is inhibited to result in the failure of oncolysis because p53 inactivation is not induced, whereas it actively proliferates in tumor cells with inactivated p53 and eventually leads to selective death of tumor cells (Chang, F., et al., *J Clin Oncol* 13:1009-22(1995)).

According to recent reports on Phase-II/III clinical trials for brain cancer, a tumor-specific oncolytic adenovirus exhibits considerable therapeutic efficacy (Kirn, D., et al., *Nat Med* 4:1341-2 (1998); Nemunaitis, J. et al., *Cancer Res* 60:6359-66 (2000); and Ganly, I. et al., *Clin Cancer Res* 6:798-806 (2000)). Although the administration of the recombinant adenovirus induces the partial suppression of tumor growth, the complete eradiation of tumor does not been found and regrowth of tumor rapidly occurs after the lapse of a period of time. Theses results are probably because the recombinant adenovirus topically injected into tumor are partially spread within a limited surrounding portion to elicit a restricted anti-tumor activity such that tumor cells not infected with viruses rapidly grow. According to a recent research report, the recombinant adenoviruses administered into human tumor in nude mice persistently replicate as late as 100 days after initial viral injection and do not ensure the complete eradication of tumor, while viable viruses may be obtained from tumor tissue. According to subsequent research reports, it has been clarified that those low anti-tumor effects are because the connective tissue and extracellular matrix (ECM) present in cell play a prominent role in inhibiting viral spread of recombinant adenoviruses. Moreover, when adenoviruses are injected into tumor, in early stage, they are rapidly eradicated from blood stream by innate immune reaction; however, on about 48 weeks after viral injection, adenoviruses presumed to be replicated in tumor and released to the blood stream could be observed to appear again in the blood stream. Taking those successive results into consideration, it could be recognized that the physical barriers such as connective tissue and extracellular matrix (ECM) between tumor cells is likely to inhibit viral spread and then to highly decrease the anti-tumor effect of adenoviruses, although tumor-specific oncolytic adenoviruses administered are actively replicated in tumor cells.

Consequently, it could be appreciated that the ideal tumor-specific oncolytic adenovirus has the ability to induce greater oncolytic activity and spread throughout tumor tissue as well for infecting surrounding tumor cells.

Recently, several investigations have been reported to conquer low transduction efficiency of viral gene carriers resulting from their limited spreading potential within tissues. N. Kuriyama et al. reported that either collagenase/dispase or trypsin to digest collagen and other components of extracellular matrix enhanced viral infection, indicating that protease pretreatment may be a useful strategy for enhancing virus-mediated gene transduction (Kuriyama N, et al., *Hum Gene Ther*, 2000, 11(16):2219-2230). Moreover, L. Maillard et al. attempted to elevate the efficiency of adenovirus-mediated gene transfer by about two-fold by treating rabbit iliac arteries with elastinase, an enzyme which dissociates elastin, which is an essential component of arteries (Maillard, L., et al., *Gene Ther.* 1998, 5(8):1023-1030). There was a report that hyaluronidase, an enzyme which dissociates extracellular matrix, could enhance the gene transduction efficiency of adeno-associated viruses in the rat muscle by about 2-3 folds (Favre D, et al., *Gene Ther,* 2000, 7(16):1417-1420). Through the results of these successive investigations, it would be understood that the decrease in extracellular components by either inhibiting the synthesis of extracellular components or facilitating the dissociation of extracellular components may increase the spreading of viruses in tissues, thereby improving the efficiency of gene transduction by viruses. Moreover, it would be recognized that obstructing extracellular matrix assembly may prevent and treat fibrotic diseases such as keloid caused by abnormal proliferation of skin connective tissues Throughout this application, several patents and publications are referenced and citations are provided in parentheses. The disclosure of these patents and publications is incorporated into this application in order to more fully describe this invention and the state of the art to which this invention pertains.

DETAILED DESCRIPTION

The present inventors have made intensive researches to improve the transduction efficiency of gene delivery systems, particularly, to enhance the transduction (or spreading) efficiency of gene delivery systems in tissues, as a result, discovering that decorin could dramatically improve the transduction efficiency of gene delivery systems and recombinant adenoviruses expressing decorin could significantly exhibit the potential to penetrate into tumor tissues and anti-tumor effect.

Accordingly, it is an object of this invention to provide a gene delivery system comprising a decorin-encoding nucleotide sequence with improved transduction efficiency.

It is another object of this invention to provide a method for delivering a gene into cells with improved transduction efficiency.

It is still another object of this invention to provide a recombinant adenovirus having improved abilities in tumor tissue penetration and tumor-specific apoptosis.

It is further object of this invention to provide a pharmaceutical anti-tumor composition for treating a cancer.

It is still further object of this invention to provide a method for treating a cancer by use of the pharmaceutical anti-tumor composition.

It is another object of this invention to provide a pharmaceutical composition for improving a penetration potency of a medicament into a tissue.

It is still another object of this invention to provide a pharmaceutical composition for treating a disease or condition associated with accumulation of excess extracellular matrix.

Other objects and advantages of the present invention will become apparent from the detailed description to follow taken in conjugation with the appended claims and drawings.

In one aspect of this invention, there is provided a gene delivery system comprising a nucleotide sequence of interest to be delivered into a cell, the improvement which comprises a decorin-encoding nucleotide sequence to enhance a transduction efficiency of the nucleotide sequence of interest into the cell.

The present inventors have made intensive researches to improve the transduction efficiency of gene delivery systems, particularly, to enhance the transduction (or spreading) efficiency of gene delivery systems in tissues. Such researches are based on our hypothesis that the reduction in the level of components of extracellular matrix by facilitating the degradation or inhibiting the synthesis of components of extracellular matrix may enhance the spreading of gene delivery systems within tissues. Surprisingly, the present inventors have discovered that decorin could dramatically improve the transduction efficiency of gene delivery systems.

The term "decorin" used herein encompasses decorin illustrated and exemplified in Examples as well as its any homologue to enhance transduction efficiency that is intent of the present invention.

Decorin (DCN) playing a pivotal role as an enhancer in improving the gene transduction efficiency in the present invention, is a prototypic member of an enlarging family of SLRP (small leucine-rich proteoglycan), comprising 10-12 leucine-rich repeats. The core region of decorin has an arch shape to serve as a suitable ligand to various growth factors or decorin receptor present in extracelluar matrix (Krusius T, Ruoslahti E., *Proc Natl Acad Sci USA*, 1986, 83(20):7683-7687; Day A A, et al., *Biochem J*, 1987, 248(3):801-805; Fisher L W, Termine J D, Young M F., *J Biol Chem*, 1989, 264(8):4571-4576). The proteoglycan decorin is known to suppress TGF-β activity, so that it inhibits fibrosis of collagen to involve in extracellular matrix assembly, and acts as a naturally occurring antagonist against tumorigenesis and tumor growth (Iozzo R V., *Crit Rev Biochem Mol Biol*, 1997, 32(2):141-174; Isaka Y, et al., *Nat Med*, 1996, 2(4):418-423). Moreover, decorin together with extracellular matrix components such as growth factors and metal ions induces expressions of MMP-1 (matrix metalloproteinase-1) and MMP-2, degrading extracellular matrix (Yamaguchi Y, Mann D M, Ruoslahti E., *Nature*, 1990, 346(6281):281-284; Vogel K G, Paulsson M, Heinegard D., *Biochem J*, 1984, 223(3):587-597; Danielson K G, et al., *J Cell Biol*, 1997, 136(3):729-743).

According to the gene delivery system of the present invention, decorin promotes the expression of various MMPs such as MMP2 and MMP9, so that the expressed decorin induces the degradation of collagen, a major component of extracellular matrix surrounding cells to disrupt connective tissue and basal membrane, thereby resulting in the degradation of extracellular matrix. This successive action is one of mechanisms underlying the improvement in transduction efficiency by decorin, which is clearly verified in Examples described below.

Therefore, referring to the above-described action of decorin, the advantages of the present gene delivery system is highlighted for cells within tissues composed of cells interconnected each other by extracellular matrix. In particular, where applied to tumor tissues enclosed tightly by connective tissue, the present gene delivery system exhibits improved transduction efficiency compared to any conventional delivery system.

To construct the present gene delivery system, it is preferred that the decorin-encoding nucleotide sequence is contained in a suitable expression construct. According the expression construct, it is preferred that the decorin-encoding nucleotide sequence is operatively linked to a promoter. The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. According to the present invention, the promoter linked to the decorin gene is operable in, preferably, animal, more preferably, mammalian cells, to control transcription of the decorin gene, including the promoters derived from the genome of mammalian cells or from mammalian viruses, for example, U6 promoter, H1 promoter, CMV (cytomegalovirus) promoter, the adenovirus late promoter, the vaccinia virus 7.5K promoter, SV40 promoter, HSV tk promoter. RSV promoter, EF1 alpha promoter, metallothionein promoter, beta-actin promoter, human IL-2 gene promoter, human IFN gene promoter, human IL-4 gene promoter, human lymphotoxin gene promoter, human GM-CSF gene promoter, inducible promoter, tumor cell specific promoter (e.g., TERT promoter, PSA promoter, PSMA promoter, CEA promoter, E2F promoter and AFP promoter) and tissue specific promoter (e.g., albumin promoter). Most preferably, the promoter is CMV promoter or tumor cell specific promoter. As a tumor cell specific promoter, TERT promoter and E2F promoter are preferable. As a TERT (telomere reverse transcriptase) promoter, the wild type human hTERT (human telomere reverse transcriptase) promoter or m-hTERT promoter (see WO 2004/076668) developed by the present inventors may be used. The m-hTERT promoter used in the present invention has been developed to carry one or more (preferably, one) additional c-Myc binding regions and one or more (preferably, five) Sp1 binding regions as well as the human telomere reverse trancriptase promoter including two c-Myc binding regions and five Sp1 binding regions. The detailed descriptions for nucleotide sequences of the m-hTERT promoter are disclosed in WO 2004/076668. The E2F promoter used in the present invention is a promoter involved in cell cycles (Johnson, D. G., *Mol. Carcinog.* 27: 151-157 (2000); Ngwenya, S., and Safe, S., *Endocrinology* 144:1675-1685; Cam, H., and Dynlacht, D., *Cancer Cell* 3:311-316 (2003)).

Preferably, the expression construct used in this invention comprises a polyadenylation sequence (e.g., bovine growth hormone terminator and SV40-derived polyadenylation sequence).

According to a preferred embodiment, the expression construct for the decorin-encoding nucleotide sequence has a structure of "promoter-decorin-encoding nucleotide sequence-polyadenylation sequence.

In the present gene delivery system, the nucleotide sequence of interest to be delivered into cells may be contained in an expression construct having the same structure for that for the decorin-encoding nucleotide sequence.

The nucleotide sequence of interest to be delivered into cells may be any sequence, for example, including cancer-therapeutic genes encoding proteins having anti-tumor activity and eventually degenerating tumor cells such as tumor suppressor genes, immunomodulatory genes [e.g, cytokine genes, chemokine genes and costimulatory factor genes (for T cell activity such as B7.1 and B7.2)], antigenic genes, suicide genes, cytotoxic genes, cytostatic genes, pro-apoptotic genes and anti-angiogenic genes, but not limited to.

The suicide genes encode proteins capable of conferring to tumor cells sensitivity to chemotherapeutic agents, or of inducing toxic conditions in tumor cells. The most well-known suicide gene is the herpes simplex virus-thymidine kinase (HSV-TK) gene (U.S. Pat. Nos. 5,631,236 and 5,601, 818). Cells expressing HSV-TK are susceptible to selective cell death by gancyclovir. The tumor suppressor genes encode polypeptides to inhibit tumorigenesis. The tumor suppressor genes are inherent in mammalian cells and their deletion or inactivation is believed to be a prerequisite for tumorigenesis. Examples of the tumor suppressor genes include members of the tumor suppressor gene INK4 family, which are exemplified by APC, DPC4, NF-1, NF-2, MTS1, WT1, BRCA1, BRCA2, VHL, p53, Rb, MMAC-1, MMSC-2, retinoblastoma gene (Lee et al., *Nature*, 329:642 (1987)), gene of adenomatous polyposis *coli* protein (Albertsen et al., U.S. Pat. No. 5,783,666), nasopharyngeal carcinoma tumor suppressor gene that maps at chromosome 3p21.3 (Cheng et al., *Proc. Natl. Acad. Sci.*, 95:3042-3047 (1998)), deleted in colon carcinoma (OCC) gene, MTS1, CDK4, VHL, p100Rb, p16 and p21, and therapeutically effective fragments thereof (e.g., p56Rb, p94Rb). It will be understood that other known anti-tumor genes can be used by those of ordinary skill in the art.

The term "antigenic genes" as used herein, refers to a nucleotide sequence coding for antigenic cell surface protein which is recognized by the immune system. Examples of the antigenic genes include carcinoembryonic antigen (CEA), prostate specific antigen (PSA), α-feto protein (AFP) and p53 (WO 94/02167). In order to facilitate immune recognition, the antigenic gene may be fused to the MHC type I antigen.

The term "cytotoxic gene" as used herein, refers to a nucleotide sequence, the expression of which in a cell elicits a toxic effect. Examples of the cytotoxic genes include nucleotide sequences encoding *Pseudomonas* exotoxin, ricin toxin, diphtheria toxin and the like.

The term "cytostatic gene" as used herein, refers to a nucleotide sequence, the expression of which in a cell induces an arrest in the cell cycle. Examples of the cytostatic genes include, but are not limited to, p21, retinoblastoma gene, E2F-Rb fusion protein gene, genes encoding cyclin-dependent kinase inhibitors such as p16, p15, p18 and p19, growth arrest specific homeobox (GAX) gene (WO 97/16459 and WO 96/30385).

In addition, a variety of therapeutic genes useful in treating various diseases may be carried in the gene delivery system of this invention. Non-limiting examples of the therapeutic genes include genes encoding cytokines (e.g., interferon-α, interferon-β, interferon-δ and interferon-γ), interleukins (e.g., IL-1, IL-2, IL-4, IL-6, IL-7, IL-10, IL-12, IL-19 and IL-20), colony-stimulating factors (e.g., GM-CSF and G-CSF), chemokine genes [monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1α (MIP-1α), macrophage inflammatory protein 1β(MIP-1β), macrophage inflammatory protein 1γ (MIP-1γ), macrophage inflammatory protein 3α (MIP-3α), macrophage inflammatory protein 3β (MIP-3β), chemokine (ELC), macrophage inflammatory protein 4 (MIP-4), macrophage inflammatory protein 5 (MIP-5), LD78β, RANTES, SIS-epsilon (p500), thymus and activation-regulated chemokine (TARC), eotaxin, 1-309, human protein HCC-1/NCC-2, human protein HCC-3, and mouse protein C10].

In addition, the therapeutic genes include genes encoding tissue-type plasminogen activator (tPA) or urokinase-type plasminogen activator, and LAL-generating gene to provide sustained thrombolysis for preventing hypercholesterolemia. Further, nucleotide sequences available for treatment of various diseases including cystic fibrosis, adenosine deaminase deficiency, AIDS and other infectious diseases, and malignant and inflammatory diseases are known to be useful as therapeutic genes.

The term "pro-apoptotic gene" as used herein, refers to a nucleotide sequence, the expression of which results in the programmed cell death. Examples of the pro-apoptotic genes include p53, adenovirus E3-I1.6K (derived from Ad2 and Ad5) or adenovirus E3-10.5K (derived from Ad), adenovirus E4 gene, Fas ligand, TNF-α, TRAIL, p53 pathway genes and genes encoding a series of caspases.

The term "anti-angiogenic gene" as used herein, refers to a nucleotide sequence, the expression of which results in the extracellular secretion of anti-angiogenic factors. Anti-a1 giogenesis factors include angiostatin, inhibitors of vascular endothelial growth factor (VEGF) such as Tie 2 (PNAS, 1998, 95, 8795-8800), and endostatin.

The nucleotide sequences of interest described previously are available from DNA sequence databases such as Gen-Bank and EMBL.

The gene delivery system of the present invention is constructed in a variety of forms, preferably, (i) naked recombinant DNA molecule, (ii) plasmid, (iii) viral vector, or (iv) liposome or neosome containing naked recombinant DNA molecule and plasmid.

The decorin-encoding nucleotide sequence may be applied to a multitude of gene delivery systems useful in gene therapy, preferably, plasmid, adenovirus (Lockett L J, et al., *Clin. Cancer Res.* 3:2075-2080 (1997)), adeno-associated virus (AAV, Lashford L S., et al., *Gene Therapy Technologies, Applications and Regulations* Ed. A. Meager, 1999), retrovirus (Gunzburg W H, et al., Retroviral vectors. *Gene Therapy Technologies, Applications and Regulations* Ed. A. Meager, 1999), lentivirus (Wang G. et al., *J. Clin. Invest.* 104(11):R55-62 (1999)), herpes simplex virus (Chamber R., et al., *Proc. Natl. Acad. Sci USA* 92:1411-1415 (1995)), vaccinia virus (Puhlmann M. et al., *Human Gene Therapy* 10:649-657 (1999)), liposome (Methods in Molecular Biology, Vol 199, S. C. Basu and M. Basu (Eds.), Human Press 2002) or neosome. Most preferably, the gene delivery system of this invention is constructed by incorporating the decorin-encoding nucleotide sequence to adenoviruses.

(i) Adenovirus

Adenovirus has been usually employed as a gene delivery system because of its mid-sized genome, ease of manipulation, high titer, wide target-cell range, and high infectivity. Both ends of the viral genome contains 100-200 bp ITRs (inverted terminal repeats), which are cis elements necessary for viral DNA replication and packaging. The E1 region (E1A and E1B) encodes proteins responsible for the regulation of transcription of the viral genome and a few cellular genes. The expression of the E2 region (E2A and E2B) results in the synthesis of the proteins for viral DNA replication.

Of adenoviral vectors developed so far, the replication incompetent adenovirus having the deleted E1 region is usually used. The deleted E3 region in adenoviral vectors may provide an insertion site for transgenes (Thimmappaya, B. et al., *Cell*, 31:543-551 (1982); and Riordan, J. R. et al., *Science*, 245:1066-1073 (1989)). Therefore, it is preferred that the decorin-encoding nucleotide sequence is inserted into either the deleted E1 region (E1A region and/or E1B region, preferably, E1B region) or the deleted E3 region, more preferably, the deleted E3 region. The nucleotide sequence of interest to be delivered is preferably inserted into either the deleted E1 region (E1A region and/or E1B region, preferably, E1B region) or the deleted E3 region, more preferably, the deleted E1 region. The term "deletion" with reference to viral genome sequences encompasses whole deletion and partial deletion as well.

According to the most preferred embodiment, the adenoviral gene delivery system of this invention comprises both "promoter-nucleotide sequence of interest-poly A sequence" and "promoter-decorin gene-poly A sequence". The promoter-nucleotide sequence of interest-poly A sequence is preferably present in either the deleted E1 region (E1A region and/or E1B region, preferably, E1B region) or the deleted E3 region, more preferably, the deleted E1 region. The promoter-decorin gene-poly A sequence is preferably present in either the deleted E1 region (E1A region and/or E1B region, preferably, E1B region) or the deleted E3 region, more preferably, the deleted E3 region. In addition, the adenoviral gene delivery system may comprise a bicistronic expression system in which the nucleotide sequence of interest and decorin-encoding nucleotide sequence are linked each other by IRES (internal ribosome entry site) to form "promoter-nucleotide sequence of interest-poly A sequence-decorin gene-poly A sequence.

In nature, adenovirus can package approximately 105% of the wild-type genome, providing capacity for about 2 extra kb of DNA (Ghosh-Choudhury et al., *EMBO J.*, 6:1733-1739 (1987)). In this regard, the foreign sequences described above inserted into adenovirus may be further inserted into adenoviral wild-type genome.

The adenovirus may be of any of the 42 different known serotypes or subgroups A-F. Adenovirus type 5 of subgroup C is the most preferred starting material for constructing the adenoviral gene delivery system of this invention. A great deal of biochemical and genetic information about adenovirus type 5 is known.

The foreign genes delivered by the present adenoviral gene delivery system are episomal, and therefore, have low genotoxicity to host cells. Therefore, gene therapy using the adenoviral gene delivery system of this invention may be considerably safe.

(ii) Retrovirus

Retroviruses capable of carrying relatively large exogenous genes have been used as viral gene delivery vectors in the senses that they integrate their genome into a host genome and have broad host spectrum.

In order to construct a retroviral vector, the decorin-encoding nucleotide sequences and the nucleotide sequence of interest to be transferred are inserted into the viral genome in the place of certain viral sequences to produce a replication-defective virus. To produce virions, a packaging cell line containing the gag, pol and env genes but without the LTR (long terminal repeat) and Ψ components is constructed (Mann et al., *Cell*, 33:153-159 (1983)). When a recombinant plasmid containing the decorin-encoding sequence, the nucleotide sequence of interest, LTR and Ψ is introduced into this cell line, the Ψ sequence allows the RNA transcript of the recombinant plasmid to be packaged into viral particles, which are then secreted into the culture media (Nicolas and Rubinstein "Retroviral vectors," In: *Vectors: A survey of molecular cloning vectors and their uses*, Rodriguez and Denhardt (eds.), Stoneham: Butterworth, 494-513 (1988)). The media containing the recombinant retroviruses is then collected, optionally concentrated and used for gene delivery.

A successful gene transfer using the second-generation retroviral vector has been reported. Kasahara et al. (*Science*, 266:1373-1376 (1994)) prepared variants of moloney murine leukemia virus in which the EPO (erythropoietin) sequence is inserted in the place of the envelope region, consequently, producing chimeric proteins having novel binding properties. Likely, the present gene delivery system can be constructed in accordance with the construction strategies for the second-generation retroviral vector.

(iii) AAV Vector

Adeno-associated viruses are capable of infecting non-dividing cells and various types of cells, making them useful in constructing the gene delivery system of this invention. The detailed descriptions for use and preparation of AAV vector are found in U.S. Pat. Nos. 5,139,941 and 4,797,368.

Research results for AAV as gene delivery systems are disclosed in LaFace et al, *Viology*, 162:483486 (1988), Zhou et al., *Exp. Hematol*. (NY), 21:928-933 (1993), Walsh et al, *J. Clin. Invest.*, 94:1440-1448 (1994) and Flotte et al., *Gene Therapy*, 2:29-37 (1995). Recently, an AAV vector has been approved for Phase I human trials for the treatment of cystic fibrosis.

Typically, a recombinant AAV virus is made by cotransfecting a plasmid containing the gene of interest (i.e., decorin gene and nucleotide sequence of interest to be delivered) flanked by the two AAV terminal repeats (McLaughlin et al., 1988; Samulski et al., 1989) and an expression plasmid containing the wild type AAV coding sequences without the terminal repeats (McCarty et al., *J. Virol.*, 65:2936-2945 (1991)).

(iv) Other Viral Vectors

Other viral vectors may be employed as a gene delivery system in the present invention. Vectors derived from viruses such as vaccinia virus (Puhlmann M. et al., *Human Gene Therapy* 10:649-657 (1999); Ridgeway, "Mammalian expression vectors," In: *Vectors: A survey of molecular cloning vectors and their uses*. Rodriguez and Denhardt, eds. Stoneham: Butterworth, 467-492 (1988); Baichwal and Sugden, "Vectors for gene transfer derived from animal DNA viruses: Transient and stable expression of transferred genes," In: Kucherlapati R, ed. *Gene transfer*. New York: Plenum Press, 117-148 (1986) and Coupar et al., *Gene*, 68:1-10 (1988)), lentivirus (Wang G. et al., *J. Clin. Invest.* 104(11):R55-62 (1999)) and herpes simplex virus (Chamber R., et al., *Proc. Natl. Acad. Sci USA* 92:1411-1415 (1995)) may be used in the present delivery systems for transferring both the decorin gene and nucleotide sequence of interest into cells.

(v) Liposome

Liposomes are formed spontaneously when phospholipids are suspended in an excess of aqueous medium. Liposome-mediated nucleic acid delivery has been very successful as described in Nicolau and Sene, *Biochim. Biophys. Acta.* 721:185-190 (1982) and Nicolau et al., *Methods Enzymol.,* 149:157-176 (1987). Example of commercially accessible reagents for transfecting animal cells using liposomes includes Lipofectamine (Gibco BRL). Liposomes entrapping the decorin gene and nucleotide sequence of interest interact with cells by mechanism such as endocytosis, adsorption and fusion and then transfer the sequences into cells.

In another aspect of this invention, there is provided a method for delivery a gene, which comprises contacting the gene delivery system of this invention as described hereinabove to a biosample containing cells.

Where the present gene delivery system is constructed on the basis of viral vector construction, the contacting is performed as conventional infection methods known in the art. The infection of hosts using viral vectors is well described in the above-cited publications.

Where the present gene delivery system is a naked recombinant DNA molecule or plasmid, the decorin-encoding sequence and nucleotide sequence to be delivered are introduced into cells by microinjection (Capecchi, M. R., *Cell,* 22:479 (1980) and Harland and Weintraub, *J. Cell Biol.* 101:1094-1099 (1985)), calcium phosphate co-precipitation (Graham, F. L. et al., *Virology,* 52:456 (1973) and Chen and Okayama, *Mol. Cell. Biol.* 7:2745-2752 (1987)), electroporation (Neumann, E. et al., *EMBO J.,* 1:841 (1982) and Tur-Kaspa et al., *Mol. Cell Biol.,* 6:716-718 (1986)), liposome-mediated transfection (Wong, T. K. et al., *Gene,* 10:87 (1980) and Nicolau and Sene, *Biochim. Biophys. Acta,* 721:185-190 (1982); and Nicolau et al., *Methods Enzymol.,* 149:157-176 (1987)), DEAE-dextran treatment (Gopal, *Mol. Cell Biol.,* 5:1188-1190 (1985)), and particle bombardment (Yang et al., *Proc. Natl. Acad. Sci.,* 87:9568-9572 (1990)).

In still another aspect of this invention, there is provided a recombinant adenovirus, which comprises an adenoviral ITR (inverted terminal repeat) nucleotide sequence and a decorin-encoding nucleotide sequence; wherein a decorin protein expressed enhances a penetration potency of the recombinant adenovirus into a tumor tissue and apoptosis of a tumor cell infected with the recombinant adenovirus.

In the recombinant adenovirus of this invention, the decorin protein expressed increases significantly a penetration potency of the recombinant adenovirus into a tumor tissue and apoptosis of a tumor cell infected with the recombinant adenovirus, making the therapeutic efficacy of the adenovirus considerably increased.

A small portion of adenoviral genome is known to be necessary as cis elements (Tooza, *J. Molecular biology of DNA Tumor viruses,* 2nd ed. Cold Spring Harbor Laboratory, Cold Spring Harbor, N.Y. (1981)), allowing substitution of large pieces of adenoviral DNA with foreign sequences, particularly together with the use of suitable cell lines such as 293. In this context, the recombinant adenovirus comprises the adenoviral ITR sequence as an essential sequence as well as the decorin-encoding nucleotide sequence.

It is preferred that the decorin-encoding nucleotide sequence is inserted into either the deleted E1 region (E1A region and/or E1B region, preferably, EIB region) or the deleted E3 region, more preferably, the deleted E3 region. The nucleotide sequence of interest to be delivered (e.g., cytokine genes, immuno-costimulatory factor genes, apoptotic genes and tumor suppressor genes) is inserted into the recombinant adenovirus, preferably into either the deleted E1 region (E1A region and/or E1B region, preferably, EIB region) or the deleted E3 region, more preferably, the deleted E1 region (E1A region and/or E1B region, most preferably, EIB region)

In nature, adenovirus can package approximately 105% of the wild-type genome, providing capacity for about 2 extra kb of DNA (Ghosh-Choudhury et al., *EMBO J.,* 6:1733-1739 (1987)). In this regard, the foreign sequences described above inserted into adenovirus may be further inserted into adenoviral wild-type genome.

According to a preferred embodiment, the recombinant adenovirus of this invention comprises the inactivated E1B 19 gene, inactivated E1B 55 gene or inactivated E1B 19/E1B 55 gene. The term "inactivation" in conjunction with genes used herein refers to conditions to render transcription and/or translation of genes to occur non-functionally, thereby the correct function of proteins encoded genes cannot be elicited. For example, the inactivated E1B 19 gene is a gene incapable of producing the functional E1B 19 kDa protein by mutation (substitution, addition, and partial and whole deletion). The defect EIB 19 gives rise to the increase in apoptotic incidence and the defect E1B 55 makes a recombinant adenovirus tumor-specific (see Korean Pat. Appln. No. 2002-0023760).

According to a preferred embodiment, the recombinant adenovirus of this invention comprises the active E1A gene. The adenovirus carrying the active EIA gene is replication-competent. More preferably, the recombinant adenovirus of this invention comprises the inactivated E1B 19/E1B 55 gene and active EIA gene. Most preferably, the recombinant adenovirus comprises the inactivated E1B 19/E1B 55 gene, the active EIA gene and the decorin-encoding sequence in place of deleted E3 region.

According to a preferred embodiment, the recombinant adenovirus of this invention comprises inactivated E1B gene, mutated E1A gene and the decorin gene inserted into the deleted E3 region. The mutated E1A gene described hereinabove comprises mutations with substitutions at amino acid 45 Glu by Gly and amino acid 121-127 by Gly residues in the Rb (retinoblastoma protein) binding region. Since mutated Rb and p53 proteins are present and Rb-relating signal cascade is significantly damaged in tumor cells, adenoviruses lack of the binding ability to Rb are actively replicated and then kill selectively tumor cells, although the replication of adenoviruses is inhibited in normal cells by the action of Rb. Therefore, the tumor specificity of the recombinant adenoviruses having mutations in the Rb binding region described above can be greatly increased.

According to the most preferred embodiment, the recombinant adenovirus of this invention comprises a structure of "ITR-EIA-ΔEIB-promoter-decorin gene-poly A sequence" in which the promoter-decorin gene-poly A sequence is present in the deleted E3 region.

The most preferable example of the present oncolytic adenovirus has a genetic map represented by FIG. 1b.

The recombinant adenovirus of this invention shows highly improved transduction (penetration) efficiency into tumors compared to conventional anti-tumoric adenoviruses and apoptosis potency as well. These improved efficacies are ascribed mainly to decorin to effectively degrade extracellular matrix and increase apoptotic potential. Consequently, the recombinant adenovirus of this invention exhibits dramatically enhanced oncolytic effect.

Tumor tissues are not agglomerates composed solely of tumor cells but complicated structure further comprising blood vessel and normal cells. In particular, the connective tissue in tumor tissues is generally rigid and forms tight extracellular matrix surrounding tumor cells. Therefore, anticancer drugs as well as viruses cannot penetrate effectively into tumors, so that they generally exhibit a limited anti-tumor effect. Such obstacles can be overcome using the recombinant adenovirus of this invention containing the decorin gene.

As demonstrated in Examples described hereunder, the adenovirus of this invention with the inserted decorin gene actively spreads even into the center of tumor spheroids as well as their surface. For in vivo tumor tissues, the decorin-expressing adenovirus of this invention spreads widely and remotely to the distal site from injection site (needle track). The improvement in the transduction efficiency accomplished by the decorin-expressing adenovirus is obvious even to be easily differentiated with naked eyes. It could be appreciated that the improved transduction efficiency is very considerable compared to about 2-3 fold increase in transduction efficiency of pretreatment of proteases such as collagenase/dispase or trypsin, elastase to degrade elasitin or hyaluronidase to degrade extracellular matrix.

The enhanced spreading effect within tissues by decorin can greatly increase anti-tumor efficacy of tumor-specific oncolytic adenovirus. This improved anti-tumor efficacy may be exhibited in replication incompetent adenoviruses as well as replication competent adenoviruses. The enhanced ability of adenoviruses to induce apoptosis by decorin is surprising and non-anticipated.

In further aspect of this invention, there is provided a pharmaceutical anti-tumor composition for treating a cancer, which comprises (a) a therapeutically effective amount of the recombinant adenovirus described previously; and (b) a pharmaceutically acceptable carrier.

In still further aspect of this invention, there is provided a method for treating a cancer, which comprises administering to an animal the pharmaceutical anti-tumor composition of described above.

The recombinant adenovirus as an active ingredient in the pharmaceutical composition is the adenovirus of the present invention described hereinabove and therefore the above descriptions can be adapted to the recombinant adenovirus of the pharmaceutical composition. Accordingly, the common descriptions between them are omitted in order to avoid undue redundancy leading to the complexity of this specification.

To effectively elicit anti-tumor effect by recombinant adenoviruses, it is necessary that viruses proliferate and spread to neighboring cells faster than the growth rate of cancer cells to induce oncolytic effect. In addition, a successful cancer-gene therapy using adenoviruses requires enhanced safety as well as high therapeutic benefit. The decorin-expressing adenovirus of this invention increases both viral spreading and apoptosis to exhibit significantly increased anti-tumor effect. In particular, the recombinant adenovirus of this invention having deleted E1B 55 gene shows excellent tumor-specificity in cytotoxicity. For this reason, the decorin-expressing adenovirus of this invention allows to decrease a dosage for cancer therapy, reducing significantly toxicity to normal cells and undesirable immune reactions in vivo Since the recombinant adenovirus of this invention has oncolytic effect to a wide variety of tumor cells, the pharmaceutical composition of this invention is useful in treating tumor-related diseases, including brain cancer, stomach cancer, skin cancer, lung cancer, breast cancer, ovarian cancer, liver cancer, bronchogenic cancer, nasopharyngeal cancer, laryngeal cancer, esophagus cancer, pancreatic cancer, bladder cancer, prostate cancer, colon cancer, and uterine cervical cancer. The term "treatment" as used herein, refers to (i) prevention of tumorigenesis; (ii) suppression and curing of tumor-related diseases or disorders by eradicating tumor cells; and (iii) alleviation of tumor-related diseases or disorders by eradicating tumor cells. Therefore, the term "therapeutically effective amount" as used herein means an amount sufficient to achieve the pharmaceutical effect described above.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative.

The pharmaceutical composition according to the present invention may be administered via the routes used commonly in gene therapy, and preferably, administered parenterally, i.e., by intravenous, intraperitoneal, intramuscular, subcutaneous, or local administration. For example, the pharmaceutical composition may be administered intraperitoneally to treat ovarian cancer and intravenously to treat liver cancer, directly injected to visible tumor mass to treat breast cancer, brain cancer, and head and neck cancer, directly injected to enema to treat colon cancer, and directly injected to a catheter to treat bladder cancer.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition, and physicians of ordinary skill in the art can determine an effective amount of the pharmaceutical composition for desired treatment. Generally, the pharmaceutical composition of the present invention comprises $1\times10^5$-$1\times10^{15}$ pfu/ml of a recombinant adenovirus, and $1\times10^{10}$ pfu of a recombinant adenovirus is typically injected once every other day over two weeks.

According to the conventional techniques known to those skilled in the art, the pharmaceutical composition comprising the recombinant adenovirus according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

The pharmaceutical composition comprising the recombinant adenovirus according to the present invention may be utilized alone or in combination with typical chemotherapy or radiotherapy. Such combination therapy may be more effective in treating cancer. The chemotherapeutic agents useful for the combination therapy include cisplatin, carboplatin, procarbazine, mechlorethamine, cyclophosphamide, ifosfamide, melphalan, chlorambucil, bisulfan, nikosourea, dactinomycin, daunorubicin, doxorubicin, bleomycin, plicomycin, mitomycin, etoposide, tamoxifen, taxol, transplatinum, 5-fluorouracil, vincristin, vinblastin and methotrexate. Examples of the radiotherapy useful for the combination therapy include X-ray illumination and γ-ray illumination.

In another aspect of this invention, there is provided a pharmaceutical composition for improving a penetration potency of a medicament into a tissue, which comprises (a) a decorin protein to improve the penetration potency of the pharmaceutical composition into the tissue; and (b) a pharmaceutically acceptable carrier.

The decorin protein contained the pharmaceutical composition of this invention may be obtained from natural sources and conventional DNA recombinant technologies. Furthermore, its fragments are encompassed in the present invention unless they are inactive in the degradation of extracellular matrix.

The pharmaceutical composition may be administered prior to or simultaneously with administration of certain medicament. In addition, the pharmaceutical composition may further comprise a medicament. The pharmaceutical composition of this invention degrades extracellular matrix surrounding tissues to be targeted by medicaments to enhance tissue penetration of medicaments, increasing significantly a pharmacological efficacy of medicaments.

The pharmaceutical acceptable carrier, administration route and method, and formulation for the present pharmaceutical composition are described with referring to descriptions for the pharmaceutical anti-tumor composition of this invention as discussed previously. In particular, the present pharmaceutical composition is preferably administered parenterally, e.g., by intravenous, intraperitoneal, intramuscular, subcutaneous or transdermal and local (e.g., direct injection into brain or breast tumor mass) administration. Generally, the pharmaceutical composition of this invention may be administered in a dosage of 0.0001-100 mg/kg.

The medicament to show improved tissue penetration by the pharmaceutical composition of this invention includes chemical drugs and biodrugs, preferably, drugs whose tissue penetration is deteriorated by extracellular matrix, e.g., anticancer drugs.

In still another aspect of this invention, there is provided a pharmaceutical composition for treating a disease or condition associated with accumulation of excess extracellular matrix, which comprises (a) a therapeutically effective amount of a decorin protein or a gene delivery system comprising a decorin-encoding nucleotide sequence; and (b) a pharmaceutically acceptable carrier.

The pharmaceutical composition of this invention degrades effectively extracellular matrix surrounding tissues to have a therapeutic efficacy on a disease or condition associated with accumulation or deposition of excess extracellular matrix. The phrase "accumulation of excess extracellular matrix" means excessive deposition of components of extracellular matrix such as collagen, laminin, fibronectin and proteoglycan to damage tissues or organs, finally causing fibrosis.

The diseases or conditions associated with excessive accumulation of extracellular matrix to be treated by the present pharmaceutical composition include fibrosis-related diseases, but not limited to, scar, liver cirrhosis, pulmonary fibrosis, glomerular nephritis, adult or acute dyspnea, hepatic fibrosis, renal fibrosis, mycocardial fibrogenesis following myocardial infarction, fibrocystic disorder, fibrotic cancer, veno-occlusive syndrome and renal stroma fibrosis.

Both scar caused by wound, burn or operation and excessive scar such as keloid may be treated with the pharmaceutical composition of this invention.

The gene delivery system comprising a decorin-encoding nucleotide sequence can be described with referring to descriptions of the gene delivery system of this invention discussed hereinabove. The decorin protein contained the pharmaceutical composition of this invention may be obtained from natural sources and conventional DNA recombinant technologies. Furthermore, its fragments are encompassed in the present invention unless they are inactive in the degradation of extracellular matrix.

The pharmaceutical acceptable carrier, administration route and method, and formulation for the present pharmaceutical composition are described with referring to descriptions for the pharmaceutical anti-tumor composition of this invention as discussed previously. In particular, the present pharmaceutical composition is most preferably administered by transdermal administration. The formulations suitable in the present pharmaceutical composition include ointment, gel, cream, solution, spray, patch and lotion. Generally, the pharmaceutical composition of this invention may be administered in a dosage of 0.0001-100 mg/kg.

The present invention provides a novel gene delivery system and recombinant adenovirus comprising the decorin-encoding sequence, a gene delivering method using the gene delivery system, a pharmaceutical anti-tumor composition comprising the recombinant adenovirus, a pharmaceutical composition characterized by improved tissue penetration potency and a pharmaceutical composition for treating a disease or disorder associated with accumulation of excess extracellular matrix. According to the present invention, decorin is responsible for the improvement in transduction efficacy and apoptotic ability to increase tumor cell killing potential dramatically.

BRIEF DESCRIPTION OF THE DRAWINGS

FIG. 1a schematically represents a genetic map of decorin expressing replication-incompetent recombinant adenoviruses (dl-LacZ, dl-LacZ-DCNG, dl-LacZ-DCNQ and dl-LacZ-DCNK) and tumor specific oncolytic recombinant adenoviruses (Ad-ΔE1B, Ad-ΔE1B-DCNG, Ad-ΔE1B-DCNQ and Ad-ΔE1B-DCNK) used in Examples. ITR, Ψ, LacZ, IX, CMV and Pol A represent inverted terminal repeat sequence, package sequence, lac Z sequence, protein IX gene, CMV promoter and poly A sequence, respectively. DCNG represents the wild type decorin gene, and DCNQ and DNCK represent mutated genes in which E180 amino acid in the leucine-rich repeat region of the wild type decorin core protein is point-mutated to E180Q, and E180K, respectively.

FIG. 1b schematically represents a more specific genetic map of the tumor specific oncolytic adenovirus Ad-ΔE1B-DCNG of the present invention.

FIG. 7a is the photograph of plates demonstrating the plaque formation in human tumor cell line, Hep3B, infected with the tumor specific oncolytic adenoviruses of this invention (Ad-ΔE1B, Ad-ΔE1B-DCNG, Ad-ΔE1B-DCNQ and Ad-ΔE1B-DCNK) and FIG. 7b is a graph demonstrating the plaque formation rate.

FIGS. 8a and 8b represent the results for tumor specific oncolytic adenoviruses (Ad-ΔE1B, Ad-ΔE1B-DCNG, Ad-ΔE1B-DCNQ and Ad-ΔE1B-DCNK) and replication-incompetent adenoviruses (dl-LacZ and dl-lacZ-DCNG), respectively. The number denotes the proportion of subG$_1$ cell population.

FIGS. 9a and 9b represent the results for tumor specific oncolytic adenoviruses (Ad-ΔE1B, Ad-ΔE1B-DCNG, Ad-ΔE1B-DCNQ and Ad-ΔE1B-DCNK) and replication-incompetent adenoviruses (dl-LacZ and dl-lacZ-DCNG), respectively. The ratios of Annexin V$^+$/PI$^-$ are indicated as italic bold letters in right bottom quadrant.

FIGS. 10a and 10b represent the results for tumor specific oncolytic adenoviruses (Ad-ΔE1B, Ad-ΔE1B-DCNG, Ad-ΔE1B-DCNQ and Ad-ΔE1B-DCNK) and replication-incompetent adenoviruses (dl-LacZ and dl-lacZ-DCNG), respectively. The DNA fragmentation was observed as brown color.

Figure 2:
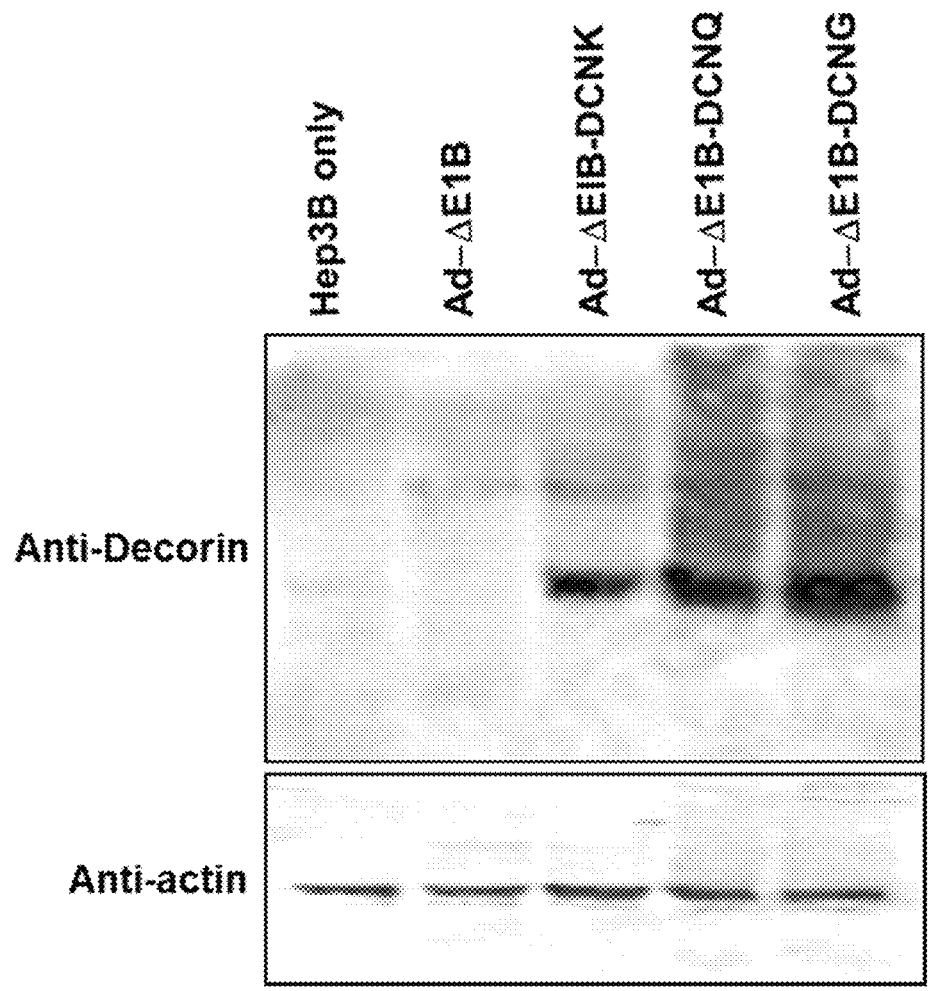
FIG. 2 is a photograph showing the results of Western blot analysis indicating that the tumor cell line, Hep3B infected with the decorin-expressing tumor specific oncolytic adenovirus of this invention (Ad-ΔE1B-DCNG, Ad-ΔE1B-DCNQ and Ad-ΔE1B-DCNK) expresses the decorin protein.

The following specific examples are intended to be illustrative of the invention and should not be construed as limiting the scope of the invention as defined by appended claims.

EXAMPLES

Materials and Methods

1. Cell Lines and Cell Culture

Cell lines for experiments were tumor cell lines such as human brain cancer cell lines (U343, U87MG), cervical cancer cell line (C33A), liver cancer cell line (Hep3B), lung cancer cell line (A549) and mouse melanoma (B16BL6), human normal cell lines (CBHEL, MRC5, IMR90 and W138) and 293 cell line carrying the early gene of adenovirus, E1 region. All cell lines except B16BL6 cell line were available from the ATCC (American Type Culture Collection; Manassas, Va., USA), and B16BL6 mouse melanoma cell line was gifted from Dr. Y. S. Park's research group at the Yonsei University of Korea.

All cell lines except B16BL6 cell line were cultured in Dulbecco's modified Eagle's medium (DMEM; Gibco BRL) supplemented with 10% fetal bovine serum (Gibco BRL), penicillin and streptomycin and maintained at 37° C. under 5% $CO_2$ atmosphere. B16BL6 cell line was cultured in RPMI medium (Gibco BRL) supplemented with 10% fetal bovine serum (Gibco BRL), penicillin and streptomycin and maintained at 37° C. under 5% $CO_2$ atmosphere.

2. Experimental Animals

In vivo anti-tumor experiments were conducted using 6- to 8-week-old male nude mice (BALB/c-nu) and C57BL/6 mice purchased from Charles River Korea (Seoul, Korea). Mice were maintained under controlled lighting cycle (12-hr light:12-hr dark), temperature (22±2° C.) and humidity (55-60%), and had free access to radiation-sterilized solid feeds (Orient, Seoul, Korea) and water.

3. Generation and Titration of Recombinant Adenoviruses Expressing Decorin

<1> Generation of Replication-Incompetent Adenoviruses

We generated EVE3-gene deleted replication-incompetent adenoviruses expressing the decorin gene and the reporter gene lac Z. The pdl-LacZ viral vector was prepared by inserting the lac Z gene as a reporter into the deleted E1 region in the vmdl324Bst vector (gifted from Dr. Verca, University of Fribourgh, Switzerland; Heider, H. et al., *Biotechniques*, 28(2):260-265, 268-270 (2000)). For preparing this vector, the pcDNA-hygro-LacZ plasmid (Invitrogen, Carlsbad, Calif., USA) was digested with HindIII and NaeI to isolate the CMV promoter, lacZ gene and polA and the isolated three sequences were inserted into the E1 adenoviral shuttle vector, pΔE1sp1A to prepare pΔE1sp1A/CMV-LacZ shuttle vector. The prepared pΔE1sp1A/CMV-LacZ shuttle vector was digested with XmnI and cotransformed with vmdl324Bst adenovirus linearized by BstBI into *E. coli* BJ5183 (Dr. Verca. University of Fribourgh, Switzerland) to induce homologous recombination, obtaining pdl-LacZ adenovirus.

For constructing decorin-expressing adenoviruses, we constructed the pcDNA3.1-DCNG (containing the wild type decorin cDNA) by inserting the decorin gene (DCNG, D. G. Seidler, University Hospital of Munster, Germany) into the expression vector pcDNA3.1. Then, the decorin mutant DCNQ having weaker binding affinity to collagen was prepared by inducing a point mutation of E180 amino acid to E180Q in the sixth leucine-rich repeat of the wild type decorin core protein, followed by inserting the mutant gene into the pcDNA3.1 vector to give the expression vector pcDNA3.1-DCNQ. In addition, the decorin mutant DCNK lack of binding affinity to collagen was prepared by inducing a point mutation of E180 amino acid to E180K of the wild type decorin core protein, followed by inserting the mutant gene into the pcDNA3.1 vector to give the expression vector pcDNA3.1-DCNK. Each of the vectors prepared above was digested with EcoRI and XbaI to give a 1 kb DNA fragment, which was inserted into the pCA14 vector (Microbix, Ontario, Canada) to generate pCA14-DCNG, pCA14-DCNQ and pCA14-DCNK vectors.

Each of the pCA14-DCNG, pCA14-DCNQ and pCA14-DCNK vectors thus prepared was digested with BglII to obtain the CMV-DCN-polA expression cassette expressing the decorin gene under the control of the CMV promoter, after which the cassette was inserted into the adenoviral E3 shuttle vector, pSP72ΔE3, to obtain the adenoviral E3 shuttle vectors, pSP72ΔE3-DCNG, pSP72ΔE3-DCNQ and pSP72ΔE3-DCNK.

The adenoviral E3 shuttle vectors thus prepared were linearized with PvuI or XmnI and cotransformed into *E. coli* BJ5183 together with the adenoviral total vector, pdl-LacZ linearized with SpeI for homologous recombination, generating the adenoviral vectors dl-LacZ-DCNG, dl-LacZ-DCNQ and dl-LacZ-DCNK which express the lac Z gene and decorin simultaneously (FIG. 1a).

<2> Generation of Tumor-Specific Oncolytic Adenovirus

We generated tumor-specific oncolytic adenoviruses expressing the decorin gene. Specifically, each of dl-LacZ-DCNG, dl-LacZ-DCNQ and dl-LacZ-DCNK was linearized with PvuI or XmnI and cotransformed into *E. coli* BJ5183 together with the E1B 19 kDa/E1B 55 kDa-deleted pAdΔE1B19/55 adenovirus vector linearized with SpeI (KFCC 11288) for homologous recombination, generating the Ad-ΔE1B-DCNG, Ad-ΔE1B-DCNQ and Ad-ΔE1B-DCNK adenovirus vectors, respectively (FIGS. 1a and 1b). To verify the occurrence of homologous recombinants, the recombinant adenoviral vectors were digested with HindIII. The proper homologous recombinant adenoviral vectors were digested with PacI and transfected into 293 cell lines to generate adenoviral vectors (FIGS. 1a and 1b).

All adenoviruses were propagated in 293 cells and their titration was performed according to limited dilution or plaque assay (Hitt, M. et. al., *Construction and propagation of human adenovirus vectors. Cell biology: a laboratory handbook*. New York: Academic Press Inc, 479-490 (1994)), followed by concentration using CsCl gradient and purification.

4. Examination of Decorin Expression Pattern

To examine the decorin expression pattern induced by recombinant adenoviruses of the present invention, tumor-specific oncolytic adenoviruses having the decorin gene (Ad-ΔE1B-DCNG, Ad-ΔE1B-DCNQ and Ad-ΔE1B-DCNK) and Ad-ΔE1B adenovirus as a control were infected to the human liver cancer Hep3B at 3 MOI. At 48 hr after infection, the medium used was recovered and subjected to SDS-PAGE (sodium dodecyl sulfate polyacrylamide gel electrophoresis). Then, the proteins on the gel were electrotransferred to PVDF membrane, incubated with the primary anti-decorin antibody (D. G. Seidler, University Hospital of Munster, Germany) and anti-β-actin antibody (Sigma, St. Louis, Mo., USA), and then incubated with the HRP (horse radish peroxidase)-conjugated secondary antibody (sc-2004; Santa Cruz Biotech., Santa Cruz, Calif.), after which the expression patterns of decorin were revealed using the ECL detection kit (sc-2004; Santa Cruz Biotech).

5. Comparable Evaluation of Transduction Efficiency

To evaluate the transduction efficiency of replication-incompetent adenoviruses expressing LacZ, various human tumor cell lines (U343, U87MG, C33A, Hep3B and A549) and human normal cell lines (CBHEL, IMR90 and W138) were plated onto 24-well plates and infected with dl-LacZ, dl-LacZ-DCNG, dl-LacZ-DCNQ or dl-LacZ-DCNK viruses at an MOI (multiplicity of infection) of 0.1-100. On day 2 after infection, the cell lines were incubated with X-Gal reagent (PBS containing 1 mg/ml, 5 mM $K_3Fe(CN)_6$, 5 mM $K_4Fe(CN)_6$ and 2 mM $MgCl_2$) at 37° C. for 6 hr for X-gal staining to confirm the transduction efficiency of the LacZ gene induced by the expression of the decorin gene.

6. Evaluation on Spreading and Penetration of Adenovirus in Tumor Spheroid

U343, U87MG, C33A and A549 xenografts were established subcutaneously by injecting cells into the abdomen of 6- to 8-week-old nude mice and once the tumors reached to 150-200 $mm^3$ in volume, fresh tumor tissue was extracted at surgery, 1-2 mm fragments of the tumor tissue were dissected. These explants were plated individually on 0.75% agarose-coated plates and cultured in DMEM (Gibco BRL) supplemented with 5% FBS (Gibco BRL) and penicillin/streptomycin (Gibco BRL) at 37° C. under 5% $CO_2$ atmosphere. Medium was renewed once every week. Prior to infection with adenoviruses, spheroids with diameter of 2 mm were transferred to 0.75% agarose-coated 48-well plates and 150 µl of DMEM (containing 5% FBS) were added, after which viruses were added at $1\times10^6$, $1\times10^7$, or $1\times10^8$ PFU (plaque-forming unit). 3-days later, the medium was aspirated and spheroids were fixed in a fixation solution for X-gal staining. The surface of X-gal stained spheroids was observed under a stereoscopic microscope (Olympus optical Co., LTD, Tokyo, Japan). For the observation on penetration of adenovirus into tumor spheroid, the X-gal stained tumor spheroids were embedded in O.C.T. compound (Sakura Finetec, Torrance, Calif.) and snap frozen. 10 µm frozen section was then placed onto gelatin-coated slide glass. Moreover, the ratio of X-gal stained portion in tumor spheroid was given using the MetaMorph program (Meta imaging series, Version 6.1, Universal imaging corporation TM, Downingtown, Pa.).

7. Evaluation on Spreading and Penetration of Adenoviruses In Vivo

U343, U87MG, C33A, and Hep3B xenografts were established subcutaneously by injecting cells into the abdomen of 6- to 8-week-old nude mice and once the tumors reached to 150-200 mm$^3$ in volume, mice were randomized into two groups and dl-LacZ and dl-LacZ-DCNG adenovirus at $5\times10^7$-$1\times10^8$ PFU was intratumorally injected five times into the tumors. For A549 xenograft model, A549 cell line was subcutaneously injected into mice and once the tumors reached to 150-200 mm$^3$ in volume, each of dl-LacZ, dl-LacZ-DCNG, dl-LacZ-DCNQ and dl-LacZ-DCNK at $5\times10^8$ PFU was intratumorally injected five times into the tumors. On day 3 after the last injection, animals were sacrificed and tumors were taken, after which they were fixed in 4% paraformaldehyde (PFA) at 4° C. for 4-8 hr and dehydrated in 30% sucrose solution for 12 hr. The dehydrated tumor tissues were embedded in O.C.T. compound and snap frozen, followed by performing X-gal staining described above.

8. Analysis of Cytopathic Effect (CPE)

To evaluate the oncolytic activity of decorin-expressing adenoviruses, human tumor cell lines (U343, U87MG, C33A, Hep3B and A549) and human normal cell lines (CBHEL, MRC5, IMR90 and W138) were plated onto 24-well plates and then infected with Ad-ΔE1, Ad-ΔE1B, Ad-ΔE1B-DCNG, Ad-ΔE1B-DCNQ or Ad-ΔE1B-DCNK adenovirus at MOIs 0.1-100. At the time that cells infected with any one of the viruses exhibited complete cell lysis at the low titer, the dead cells were washed out and cells on the plate were then stained with 0.5% crystal violet in 50% methanol.

9. Plaque Development Assay

To observe the change of plaque size over decorin expression, $3\times10^5$ Hep3B cells were placed to 6-well plates and infected with Ad-ΔE1B, Ad-ΔE1B-DCNG, Ad-ΔE1B-DCNQ and Ad-ΔE1B-DCNK adenovirus at $1\times10^{-4}$ MOI after one day of cell growth. After 4 hr of incubation, the infected cells were overlayed with agarose-DMEM mixture of 2×DMEM (containing 10% FBS and penicillin/streptomycin) at 37° C. and 1.4% UltraPure™ agarose (Invitrogen, Carlsbad, Calif.) at 42° C. and then incubated. Following about 4-16 days of incubation, the size of plaques formed on plates was observed, agarose overlay was removed by soaking with 1 ml of 10% trichloroacetic acid for 30 minutes and the remaining cells were stained with 0.5% crystal violet in 50% methanol. The number of plaques formed was counted.

10. Flow Cytometry Analysis for Apoptosis Potential

To examine apoptosis induced by decorin, human tumor cell lines, U343, U87MG, C33A, Hep3B and A549 were introduced to 25 T culture flasks and 24 hr later, were infected with each adenovirus at MOIs of 0.5-50. Cells were treated with 0.1-1 µM CPT-11 (camptothecin-11) as a positive control and treated with PBS as a negative control. After 48 hr, 72 hr and 96 hr of infection, the infected cells were collected and fixed in 70% ethanol at 4° C. over 24 hr. Following the fixation, the cells were incubated at 4° C. with a mixture of PI (propidium iodide, 50 µg/ml) and RNase (ribonuclease) for 15 min and the FACS analysis was then performed.

In addition, to examine early apoptosis induced by decorin, several human tumor cell lines were infected with each adenovirus as described above. The infected cells were collected and then processed for Annexin V/PI dual staining according to manufacturer's instruction in the ApoAlert V-FITC (fluorescein isothiocyanate) apoptosis detection kit (Clontech, Palo Alto, Calif.), followed by flow cytometric analysis.

11. TUNEL Assay

U343 ($5\times10^4$), U87MG ($5\times10^4$), C33A ($5\times10^5$), Hep3B ($4\times10^5$) and A549 ($5\times10^4$) cells were plated onto a chamber slide and then infected with adenovirus at an MOI of 0.2-20. Following 24 hr and 48 hr of infection, medium was removed and TUNNEL (terminal deoxynucleotidyl transferase (TdT)-mediated dUTP nick end labeling) assay was carried out according to the manufacturer's instruction of ApopTag kit (Intergen, Purchase, N.Y.). For color development, cells were incubated with peroxidase-conjugated avidin and DAB (diaminobenzidine; DAKO, Carpinteria, Calif.). At the time that color of cells became brown, cells were counterstained with 0.5% methyl green for 10 min and observed under microscope in more than 4 selected fields. The ratio of stained cells to total cells was calculated.

12. Anti-Tumor Effects and Survival Rates of Decorin-Expressing Adenovirus In Vivo The effect of decorin-expressing adenoviruses on the growth of human tumor spheroid formed in nude mice was assessed. Tumors were implanted on the abdomen of 6- to 8-week-old nude mice (Charles River Japan Inc.) by subcutaneous injection of $1\times10^7$ human cancer cell lines (U343, U87MG, C33A, Hep3B and A549) in 100 µl of HBSS (Hanks' balanced salt solution, Gibco BRL). When tumors reached to 50-80 mm$^3$ in volume, adenoviruses at $1\times10^8$-$5\times10^8$ PFU were administered intratumorally three times every other day and the growth pattern and survival rate of tumors were observed. The volume of tumors was calculated with the major axis and minor axis measured using a caliper: tumor volume=(minor axis mm)$^2$×(major axis mm)×0.523.

13. Observation of the Change of Tumor Characteristics Induced by the Administration of Decorin-Expressing Replication-Competent Adenoviruses When U343, U87MG, C33A, Hep3B or A549 tumor formed in the abdomen of nude mice reached to about a range of 50-80 mm$^3$, adenoviruses at $1\times10^8$-$5\times10^8$ PFU were administered intratumorally three times. Following 3 days of injection, the tumor tissues were extracted and their paraffin blocks were prepared. The blocks were cut into 3-1 µm slides and deparaffinized in xylene and then in graded alcohols (100%, 95%, 80% and 70%), followed by staining with hematoxylin and eosin. For the observation of distribution of collagen, a component of connective tissue, 3-µm paraffin-embedded slides were stained using bouin, hematoxylin and biebrich's scarlet acid fuchsin. The staining reagents were purchased from DAKO ARK (Dako, Carpinteria, Calif.). In addition, the immunohistochemistry staining for the hexon region of adenoviruses was carried out. The slides were deparaffinized as described above and incubated with the primary anti-adenoviral hexon antibody (MAB 8052 chemicon, Temecula, Calif.) and then with the secondary goat anti-rat IgG-HRP (Santa Cruz Biotechnology, Inc., Santa Cruz, Calif.). The color development was performed using DAB (DAKO, Carpinteria, Calif.).

To observe the occurrence of apoptosis in tumors, TUNNEL assay was carried out according to the manufacturer's instruction of ApopTag kit (Intergen, Purchase, N.Y.). For the color development, cells were incubated with peroxidase-conjugated avidin and then DAB (DAKO, Carpinteria, Calif.). At the time that color of cells became brown, cells were counterstained with 0.5% methyl green for 10 min and observed under microscope.

14. Examination for Expression Pattern of MMP by Zymoaraphy

To observe the change of MMP activity, various human tumor cell lines (U343, U87MG, C33A, Hep3B and A549) were introduced to 75 T culture flasks and 24-hr later, were infected with PBS, Ad-ΔE1B or Ad-ΔE1B-DCNG adenovirus at an MOI 1-100 and then, incubated for 48 hours. The cells were additionally incubated for 24 hr in refreshed DMEM without FBS, and the medium was collected and concentrated. The proteins present in the medium were quantified using the protein analysis kit (Bio-Rad, Hercules, Calif., USA) and their same amounts were electrophoresed on a gelatin-substrate gel. After the electrophoresis, the gel was subject to gelatinolysis at 37° C. for 18 hr, and stained with Coomassie brilliant blue to observe the expressions of MMP-2 and MMP-9. In addition, each experiment was independently conducted three times and the thickness of bands formed were compared by QuntityOne2.1 program (BIO-Rad Laboratories, Hercules, Calif.).

15. Changes of Metastatic Potential Over Decorin Expression Using Spontaneous Metastasis Model To assess changes of metastatic potential over decorin overexpression, B16BL6 cells ($2 \times 10^5$/mouse) were administered subcutaneously into the right hind foot pad of 6-8-week-old male C57BL/6 mice (Charles River Korea, Seoul, Korea) to form primary tumors. Once the primary tumor reached to 100-200 mm$^3$ in volume, PBS, Ad-ΔE1B or Ad-ΔE1B-DCNG were injected directly into tumors three times every other day. On day 5 after the last injection, the primary tumors were surgically removed by amputating below knee under mild anesthesia. On day 20 following primary tumor removal, the weight of metastatic tumor lesions in the lungs of the mice was assessed.

16. Evaluation on Transduction Efficiency and Tissue Penetration Potency of Decorin-Expressing Adenoviruses Using Tumor Tissues from Breast Cancer Patient Tumor tissues and adjacent normal tissues from breast cancer patients were collected, cut into 1-2 mm sections and then plated onto 24-well plates, after which they were cultured for 4 hr in IMDM (Isocove's Modified Dulbecco's Medium) supplemented with 5% FBS, 10 μM/L insulin and 1 μM/L hydrocortisone. Each of dl-LacZ and dl-LacZ-DCNG adenoviruses at $1 \times 10^8$ PFU were added into the plates containing breast tumor and normal tissues, and incubated at 37° C. in 5% $CO_2$ incubator for 5 days. Following the incubation, the medium was removed from the plates, and breast tumor and normal tissues were fixed in a fixation solution and X-gal stained. The surface of X-gal stained tumor tissues was observed under a stereoscopic microscope (Olympus optical Co., LTD, Tokyo, Japan).

17. Evaluation on Transduction Efficiency of Decorin-Expressing Adenovirus in Primary Keloid Cells The primary keloid cell line at passage 2 obtained from keliod patients was plated onto 24-well plates and then infected with dl-LacZ or dl-LacZ-DCNG adenovirus at an MOI of 0.1-50, followed by incubating at 37° C. in 5% $CO_2$ incubator. At 48 hr of viral infection, cells were X-gal stained to reveal the transduction efficiency of adenoviruses.

18. Evaluation on Spreading and Penetration Potency Using Keloid Spheroid Model

The primary keloid cells ($1 \times 10^5$) at passage 2 from keliod patients were added into a 15 ml falcon tube and centrifuged at 500×g for 5 min to obtain keloid spheroid, followed by culturing at 37° C. for 5 days. The keloid spheroid was transferred to 0.75% agarose-coated 48-well plate and 150 μl of DMEM (containing 5% FBS) were added, after which dl-LacZ or dl-LacZ-DCNG adenoviruses at $1 \times 10^7$ PFU was added to the medium. Following 3 days of viral infection, the keolid spheroid was fixed in a fixation solution and X-gal stained. The X-gal stained spheroids was observed under a stereoscopic microscope.

19. Evaluation on Spreading and Penetration Potency to Tissues from Keloid Patients The keloid tissues were extracted from keliod patients and dissected to 1-2 mm sections. The sections were cultured in 0.75% agarose-coated incubator in DMEM containing 5% FBS and penicillin/streptomycin. The medium used was refreshed once or twice every week and the keloid tissues were cultured for more than one week. Keloid tissues in a diameter of 2 mm were transferred to 0.75% agarose-coated 48-well plate and 150 μl of DMEM (containing 5% FBS) were added, followed by the infection with $1 \times 10^8$ PFU dl-LacZ or dl-LacZ-DCNG adenoviruses. Following 3 days of viral infection, the keolid tissue was fixed in a fixation solution and X-gal stained. The surface of X-gal stained tissues was observed under a stereoscopic microscope. To evaluate the spreading and penetration potency of adenoviruses into tissues, the X-gal stained keloid tissues were embedded in O.C.T. compound and snap frozen. 10 μm frozen section was then placed onto gelatin-coated slide glass for microscopic observation.

RESULTS

1. Construction of Decorin-Expressing Adenoviruses and Expression Pattern of Decorin To visually evaluate the alteration of penetration efficiency into tissues depending on decorin expression, replication-incompetent dl-LacZ-DCNG, dl-LacZ-DCNQ and dl-LacZ-DCNK adenoviruses expressing LacZ as a reporter were constructed. Furthermore, tumor-specific oncolytic Ad-ΔE1B-DCNG, Ad-ΔE1B-DCNQ and Ad-ΔE1B-DCNK adenoviruses were constructed to enhance the transduction efficiency of replication-competent adenovirus into tissues (FIGS. 1a and 1b). The replication-incompetent dl-LacZ expresses lacZ gene under the control of CMV promoter which is inserted to the deleted E1 region. The tumor-specific oncolytic Ad-ΔE1B adenovirus contains normal E1A gene; however, it lacks E1B 19 kDa and E1B 55 kDa genes. The replication-incompetent dl-LacZ-DCNG, dl-LacZ-DCNQ and dl-LacZ-DCNK adenoviruses and tumor-specific oncolytic Ad-ΔE1B-DCNG, Ad-ΔE1B-DCNQ and Ad-ΔE1B-DCNK adenoviruses express the decorin gene inserted into the E3 region under the control of CMV promoter. Point mutants of decorin gene, DCNK and DCNQ contain substituted nucleotides at the region which plays a pivotal role in binding to Type I collagen fibril.

For assessing the decorin expression pattern of adenoviruses constructed, Hep3B was infected with tumor-specific oncolytic adenoviruses Ad-ΔE1B, Ad-ΔE1B-DCNG, Ad-ΔE1B-DCNQ and Ad-ΔE1B-DCNK at 3 MOIs and medium was recovered for Western blotting. Cells infected with Ad-ΔE1B as a negative control for tumor-specific oncolytic adenovirus were revealed not to express decorin, whereas all those infected with dl-LacZ-DCNG, dl-LacZ-DCNQ and dl-LacZ-DCNK showed expression of decorin (FIG. 2).

2. Comparable Evaluation of Transduction Efficiency

Figure 3A:
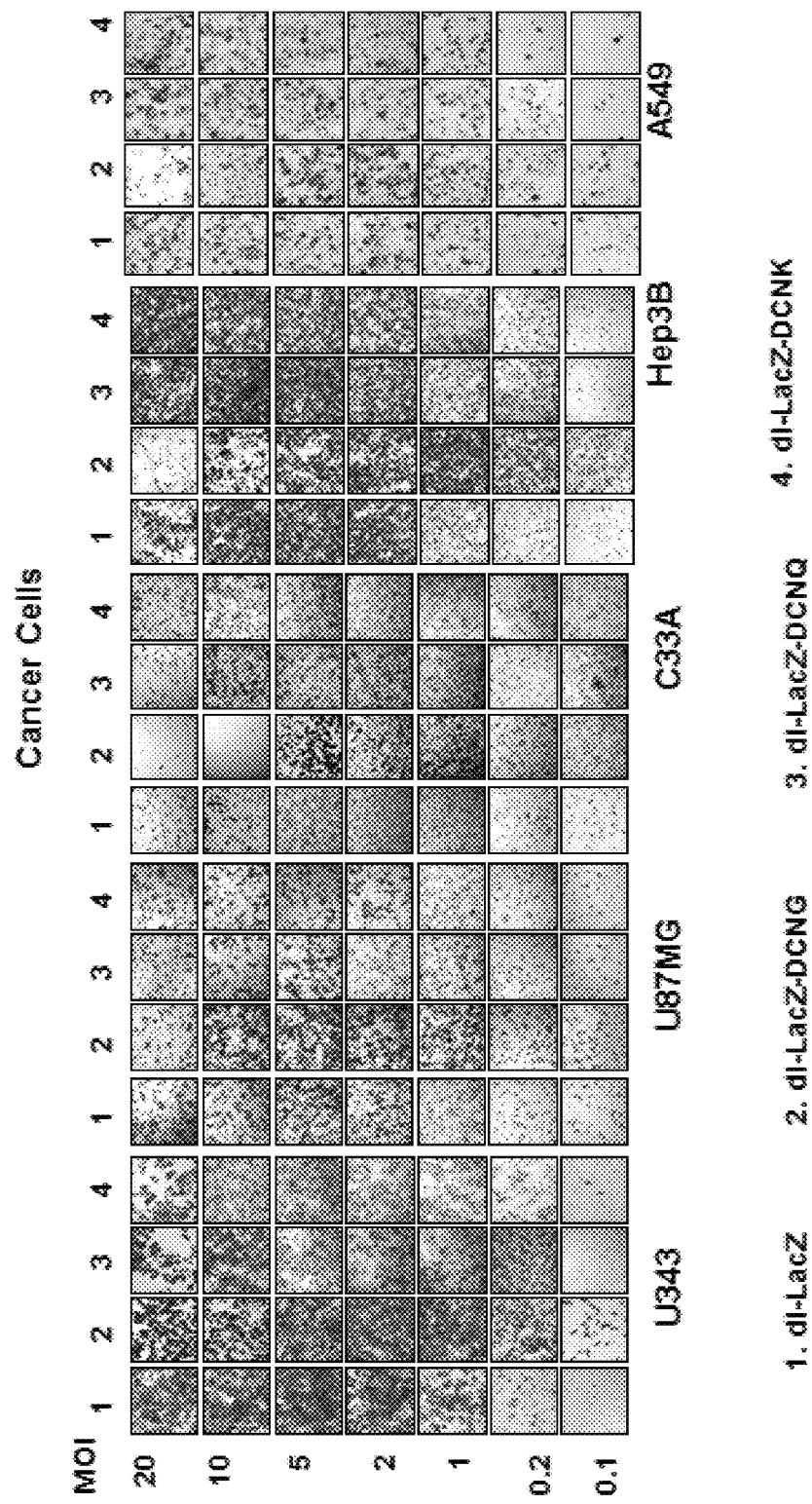
FIGS. 3a and 3b are X-gal staining images verifying the transduction efficiency of the decorin gene in human tumor cell line (FIG. 3a) and human normal cell line (FIG. 3b) that were infected with the decorin-expressing replication-incompetent adenoviruses of this invention (dl-lacZ-DCNG, dl-lacZ-DCNQ and dl-lacZ-DCNK).
Figure 3B:
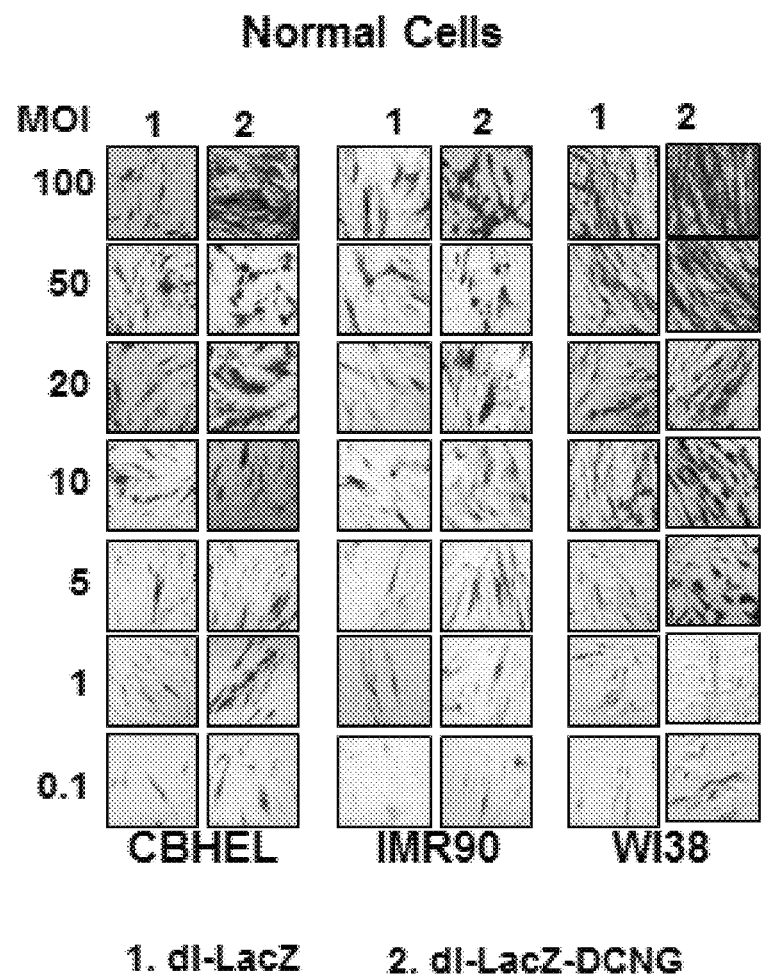

To evaluate the transduction efficiency of replication-incompetent adenoviruses, various human tumor cell lines (U343, U87MG, C33A, Hep3B and A549) and human normal cell lines (CBHEL, IMR90 and W138) were infected with each of dl-LacZ, dl-LacZ-DCNG, dl-LacZ-DCNQ and dl-LacZ-DCNK viruses at an MOI 0.1-100 and then, we observed the expression pattern of LacZ gene by performing X-gal staining after 48 hr of infection. The expression of LacZ in all tumor cell lines infected with dl-LacZ-DCNG was highly increased compared to those infected with dl-LacZ, demonstrating that the expression of decorin dramatically improves the transduction efficiency of adenovirus. Interestingly, a high titer of replication-incompetent adenoviruses showed to induce cell death. In particular, the infection with dl-LacZ-DCNG virus at MOI of no less than 10 resulted in complete cell death in C33A cells, suggesting that overexpression of decorin can successfully induce cell death (FIGS. 3a and 3b). DCNK and DCNQ having the mutated sequence at the region involved in the binding to Type I collagen fibril were expressed. The dl-LacZ-DCNQ expressing DCNQ having a weaker binding affinity to collagen exhibited slightly increased transduction efficiency compared to dl-LacZ; dl-LacZ-DCNK expressing DCNK completely lacking of the binding affinity to collagen showed nearly identical level of transduction efficiency to dl-LacZ. These results led us to reason that the expression of the wild type decorin greatly enhances the transduction efficiency of adenoviruses. To the contrary, the increase in the transduction efficiency by decorin expression was not evident in normal cells, suggesting that decorin has tumor specificity.

Figure 4:
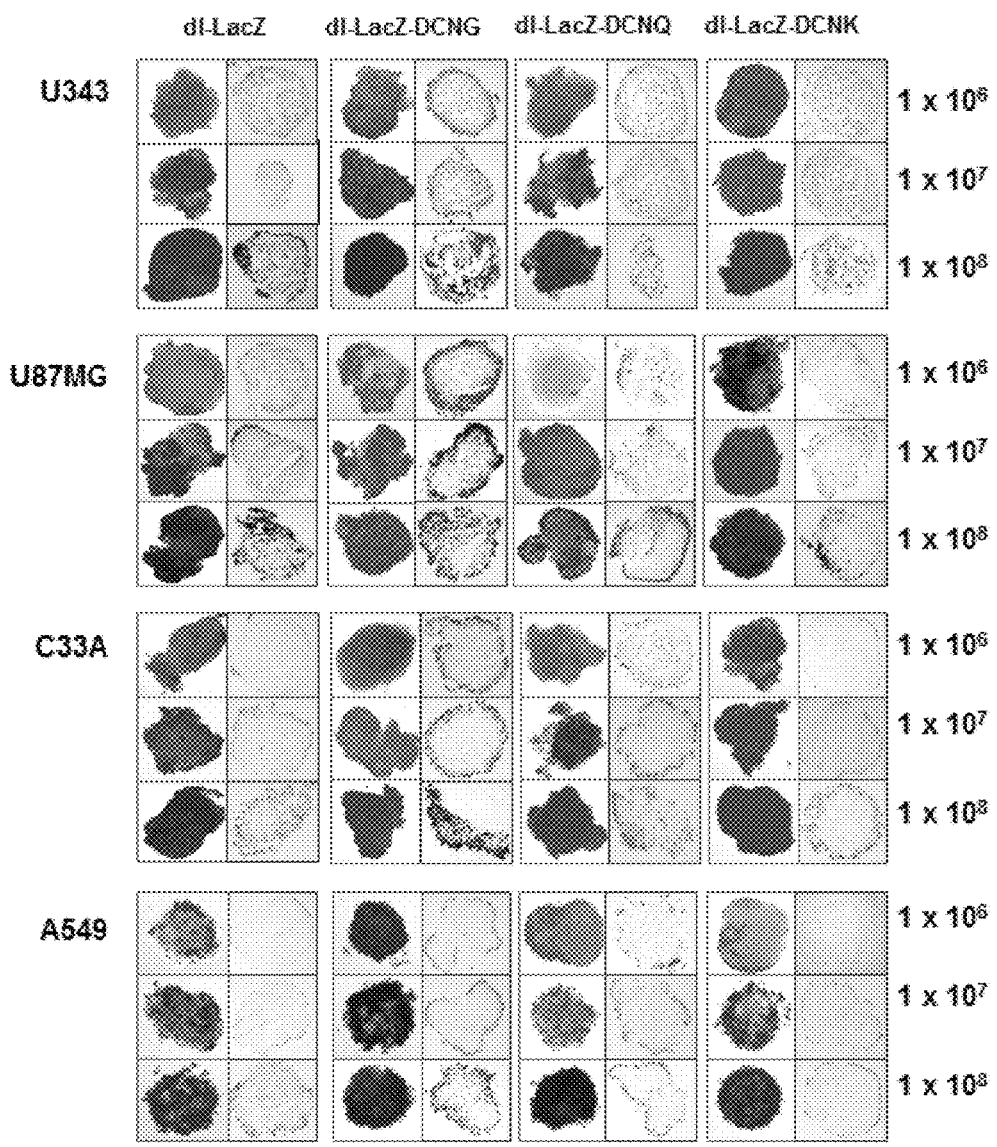
FIG. 4 is a photograph of X-gal staining representing in vitro tissue penetration of the decorin-expressing replication-incompetent adenoviruses of this invention (dl-lacZ, dl-lacZ-DCNG, dl-lacZ-DCNQ and dl-lacZ-DCNK) into tumor mass such as U343, U87MG, C33A and A549. The left panel is an optical microscope image (×38) of X-gal stained tumor mass, and the right panel, an optical microscope image (×40) of freeze-dried sections of tumor mass stained with X-gal.

3. Evaluation on Spreading and Penetration Potency of Adenovirus to In Vitro Tumor Tissue Using Tumor Spheroids To evaluate the transduction efficiency and tissue penetration potency of recombinant adenoviruses to tumor spheroids, various human tumor cell lines were subcutaneously injected into nude mice and once the tumors reached to 150-200 mm$^3$ in volume, fresh tumor tissues was extracted. The tumor tissues extracted were dissected into 1-2 mm sections and infected with adenoviruses at $1\times10^6$, $1\times10^7$, or $1\times10^8$ PFU. X-gal staining was carried out after 48 hr of infection. Compared to the treatment with dl-LacZ, dl-LacZ-DCNK and dl-LacZ-DCNQ at $1\times10^6$ PFU, the same dose of dl-LacZ-DCNG showed stronger X-gal staining on the surface of tumor spheroid. The treatment with adenoviruses of no less than $1\times10^7$ PFU led to darker X-gal staining on the overall surface of tumor spheroid (FIG. 4). To accurately investigate the penetration efficiency of adenoviruses into tumor spheroids, X-gal-stained tumor spheroids were sectioned for observation. dl-LacZ, dl-LacZ-DCNK and dl-LacZ-DCNQ at $1\times10^6$, $1\times10^7$ or $1\times10^8$ PFU exhibited poor LacZ expression in tumor tissues and its spread was limited to the surface of tumor spheroids. In contrast, the same doses of dl-LacZ-DCNG showed much higher LacZ expression level compared to dl-LacZ, dl-LacZ-DCNK and dl-LacZ-DCNQ and its spread was extended to the inner part of tumor spheroids (FIG. 4). It was recognized that the tissue penetration potency of dl-LacZ-DCNQ and dl-LacZ-DCNK is greatly decreased compared to that of dl-LacZ-DCNG. The penetration potency was decreased as the binding affinity to collagen was decreased. These results clearly demonstrate that the transduction efficiency and tissue penetration potency of dl-LacZ-DCNG to tumor spheroids are greatly increased compared to those of dl-LacZ, dl-LacZ-DCNQ and dl-LacZ-DCNK.

Figure 5:
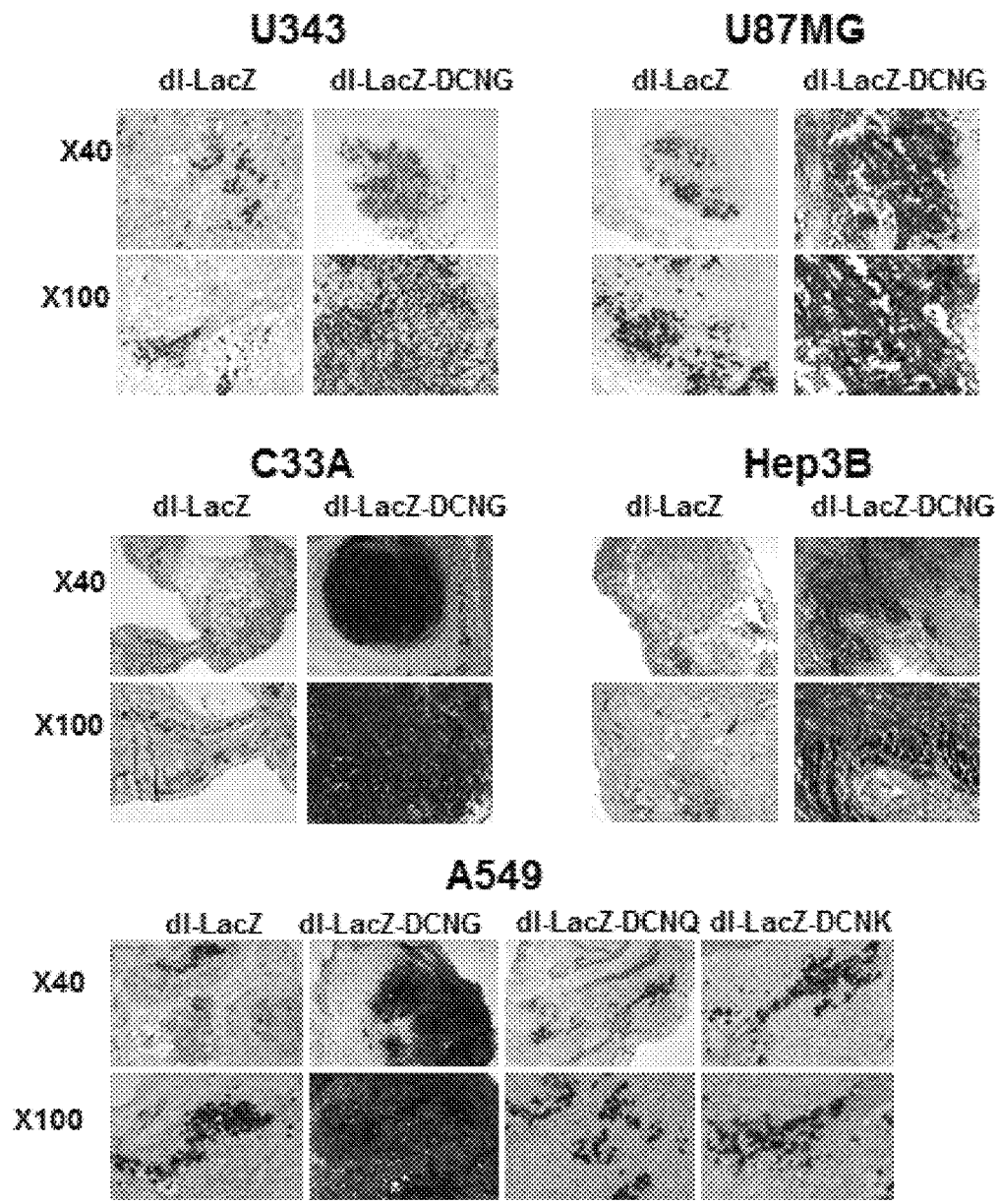
FIG. 5 represents LacZ staining results verifying the in vivo tissue penetration potential of the replication-incompetent adenoviruses of this invention (dl-lacZ, dl-lacZ-DCNG, dl-lacZ-DCNQ and dl-lacZ-DCNK) into tumor mass such as U343, U87MG, C33A, Hep3B and A549.

4. Evaluation on the Transduction Efficiency of d-LacZ-DCNG Adenovirus in Tumor Mass In Vivo In order to investigate whether the enhanced transduction efficiency and viral spread of dl-LacZ-DCNG seen in tumor spheroids in vitro would lead to an increase in gene delivery to tumor mass in vivo, tumor xenograft models were used. Each of dl-LacZ and dl-LacZ-DCNG adenoviruses at $1\times10^8$-$5\times10^8$ PFU was intratumorally injected into the tumor mass of U343, U87MG, C33A, Hep3B, and A549 formed in the abdomen of nude mice. Three days later, tumors were taken and sectioned for X-gal staining. While dl-LacZ exhibited the low level of LacZ expression and the stained region was restricted to the virus injection site, dl-LacZ-DCNG showed much higher LacZ expression and the stained region was found to be widely spread to other regions than the virus injection site (FIG. 5). In particular, U87MG and C33A tumor mass infected with dl-LacZ-DCNG showed dark blue color ascribed to intensive LacZ expression throughout all the tumor tissues. In A549 tumor xenograft model, dl-LacZ-DCNG showed much higher LacZ expression level and much deeper and wider spreading/penetration compared to dl-LacZ-DCNQ and dl-LacZ-DCNK adenoviruses. These expression profiles address that the penetration and spreading of dl-LacZ-DCNG in tumor mass in vivo is greatly enhanced compared to dl-LacZ not expressing decorin.

Figure 19A:
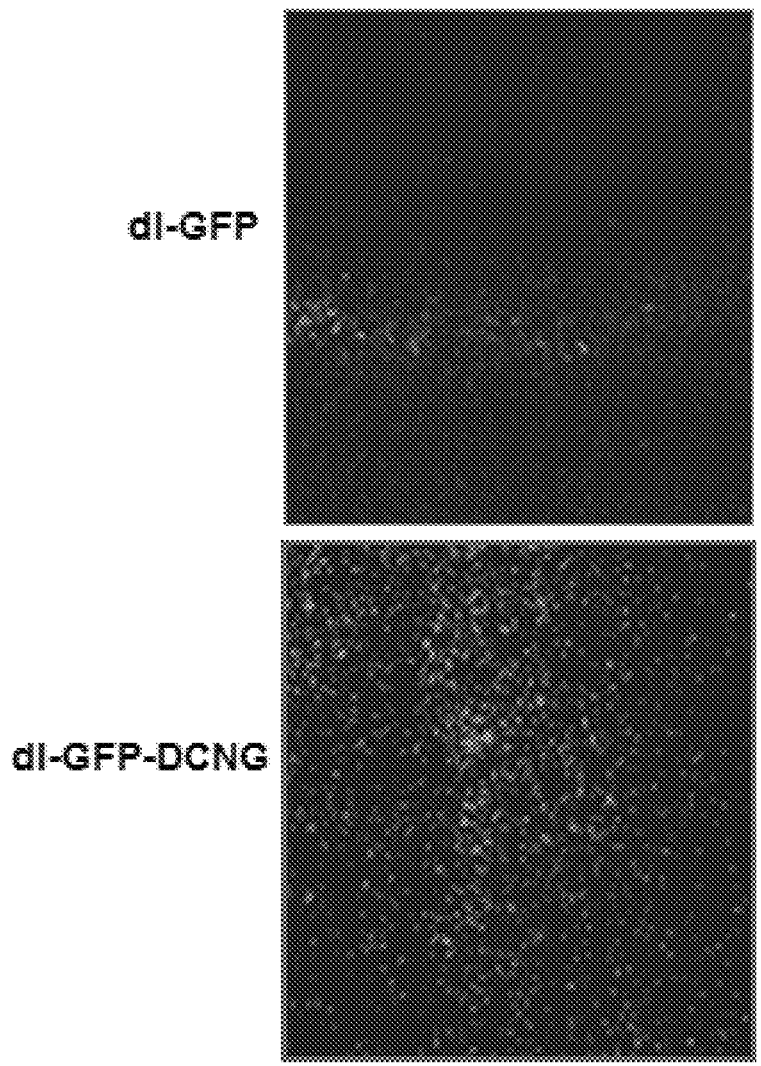
FIG. 19a is a photograph (×10) of the fluorescent microscope demonstrating the viral penetration potency of the replication-incompetent adenoviruses (dl-GFP or dl-GFP-DCNG) into C33A tumor mass established in vivo.

Furthermore, dl-GFP and dl-GFP-DCNG adenoviruses expressing GFP (green fluorescence protein) were intratumorally injected into C33A tumor mass formed in the abdomen of nude mice at $5\times10^8$ PFU. Three days later, tumors were taken and frozen sectioned for observation under fluorescent microscope. In tumor mass injected with dl-GFP, GFP was limitedly expressed along the needle track formed by viral infection; however, GFP was strongly and widely expressed in tumor mass injected with dl-GFP-DCN (FIG. 19a).

Figure 6:
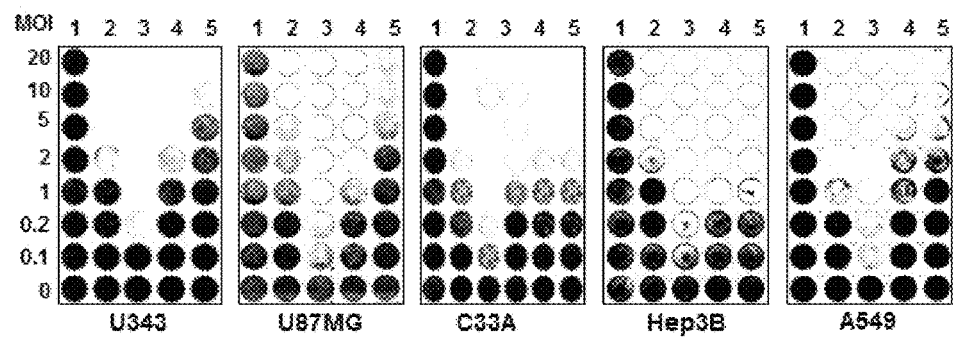
FIG. 6 represents the results of CPE (cytopathic effect) analysis demonstrating the oncolytic potency of the tumor specific oncolytic adenoviruses of this invention (Ad-ΔE1B, Ad-ΔE1B-DCNG, Ad-ΔE1B-DCNQ and Ad-ΔE1B-DCNK) in human tumor cell lines (U343, U87MG, C33A, Hep3B and A549) and human normal cell lines (CBHEL, IMR90, MRC5 and W138).
Figure 6:
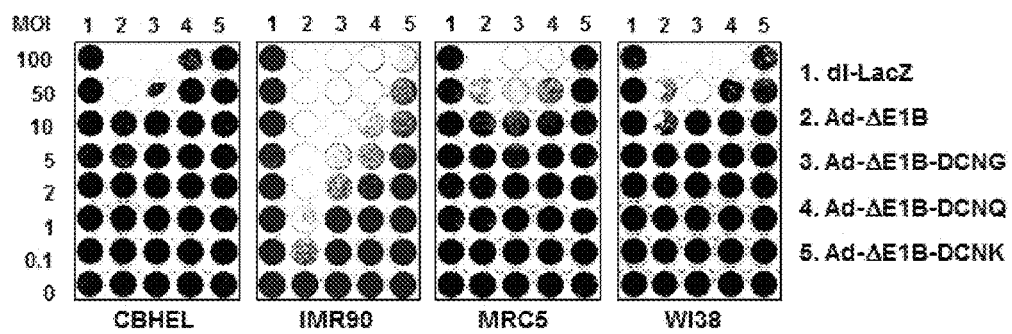

5. Assessment on Tumor Cell Killing Effect of Decorin-Expressing Oncolytic Adenovirus To reveal that the increase in penetration and spreading of decorin-expressing adenovirus contributes to enhanced tumor cell killing effect of tumor-specific oncolytic adenoviruses, a CPE assay was carried out. Each of human tumor cell lines (U343. U87MG, C33A, Hep3B and A549) and human normal cell lines (CBHEL, MRC5, IMR90 and W138) was infected with dl-LacZ (negative control), Ad-ΔE1B, Ad-ΔE1B-DCNG, Ad-ΔE1B-DCNQ and Ad-ΔE1B-DCNK adenoviruses at MOIs of 0.1-100 and the tumor cell killing effect was analyzed. As shown in FIG. 6, while the negative control, dl-LacZ elicited little or no cell killing effect in various tumor cell lines, Ad-ΔE1B-DCNG exhibited about 10-20 fold higher tumoricidal effect than Ad-ΔE1B not to express decorin. In particular, Ad-ΔE1B-DCNG adenovirus showed about 20-fold higher tumoricidal effect than Ad-ΔE1B in Hep3B and U87MG cell lines, and Ad-ΔE1B-DCNG showed about 10-fold higher tumoricidal effect than Ad-ΔE1B in U343, C33A and A549 cell lines. According to the results, it could be understood that the decorin expression does not deteriorate a replication competency of adenoviruses and contributes to the dramatic increase in tumoricidal effect of adenoviruses as well. The tumoricidal effects of Ad-ΔE1B-DCNQ and Ad-ΔE1B-DCNK were analyzed to be decreased compared to that of Ad-ΔE1B-DCNG. The tumoricidal effect was decreased upon decreasing the binding affinity to collagen. In contrast, Ad-ΔE1B-DCNG in normal cells showed little or no increase in tumoricidal effect compared to Ad-ΔE1B. Taken together, it could be appreciated that the increase in tumoricidal effect by decorin expression is induced only in tumor cells, not normal cells, which addresses tumor-specificity.

6. Plaque Formation of Decorin-Expressing Oncolytic Adenovirus

Figure 7A:
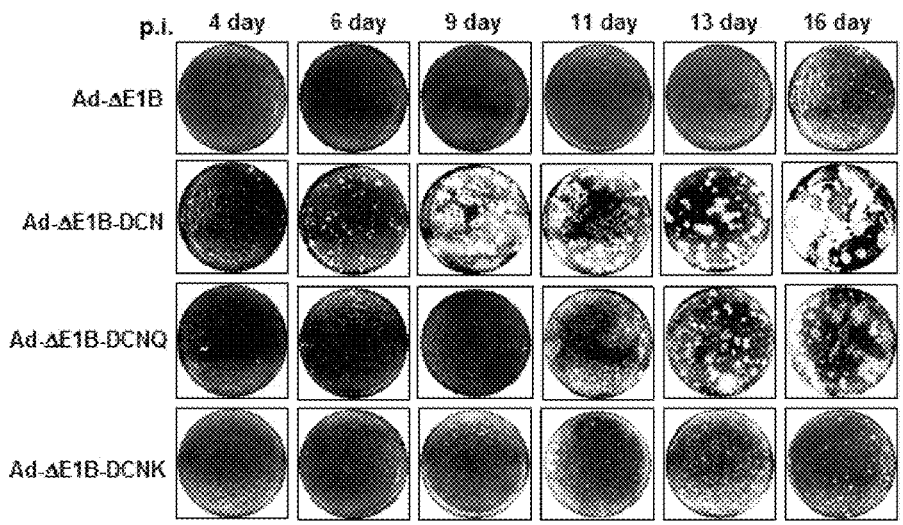
FIGS. 7a and 7b represent the results of plaque development assay.
Figure 7B:
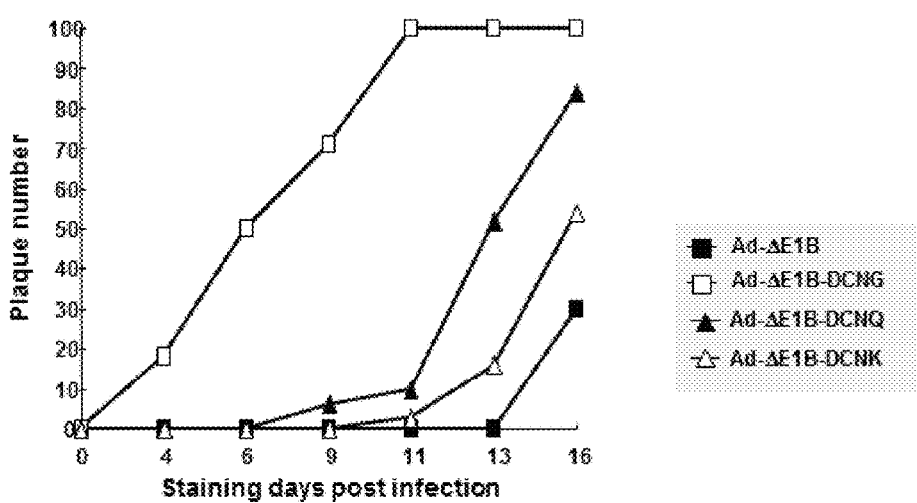

To visualize the effect of decorin expression on the cytopathic ability and viral spread into surrounding cells, plaque formation in a solid medium containing agarose was compared. Hep3B cells were infected with Ad-ΔE1B, Ad-ΔE1B-DCNG, Ad-ΔE1B-DCNQ and Ad-ΔE1B-DCNK adenoviruses and plaque formation was then analyzed. As shown in FIGS. 7a and 7b, plaques were formed in shorter time for Hep3B cells infected with Ad-ΔE1B-DCNG than those infected with Ad-ΔE1B, Ad-ΔE1B-DCNK and Ad-ΔE1B-DCNQ. In addition, plaques formed in Hep3B cells infected with Ad-ΔE1B-DCNG showed lager size than those in Hep3B cells infected with Ad-ΔE1B. More specifically, with Ad-ΔE1B, plaques were observed 13-16 days after infection, whereas plaques were formed as early as 4 days post-infection for Ad-ΔE1B-DCNG. Moreover, it is observed that the rate of plaque formation of Ad-ΔE1B-DCNQ and Ad-ΔE1B-DCNK was greatly decreased compared to that of Ad-ΔE1B-DCNG. The rate of plaque formation was decreased upon decreasing the binding affinity to collagen. These results demonstrate that the decorin-expressing adenoviruses lead to the formation of plaques in shorter period of time and much larger size owing to enhanced oncoltyic activity and viral spread to surrounding cells.

7. Apoptosis Induced by Decorin-Expressing Adenovirus

Figure 8A:
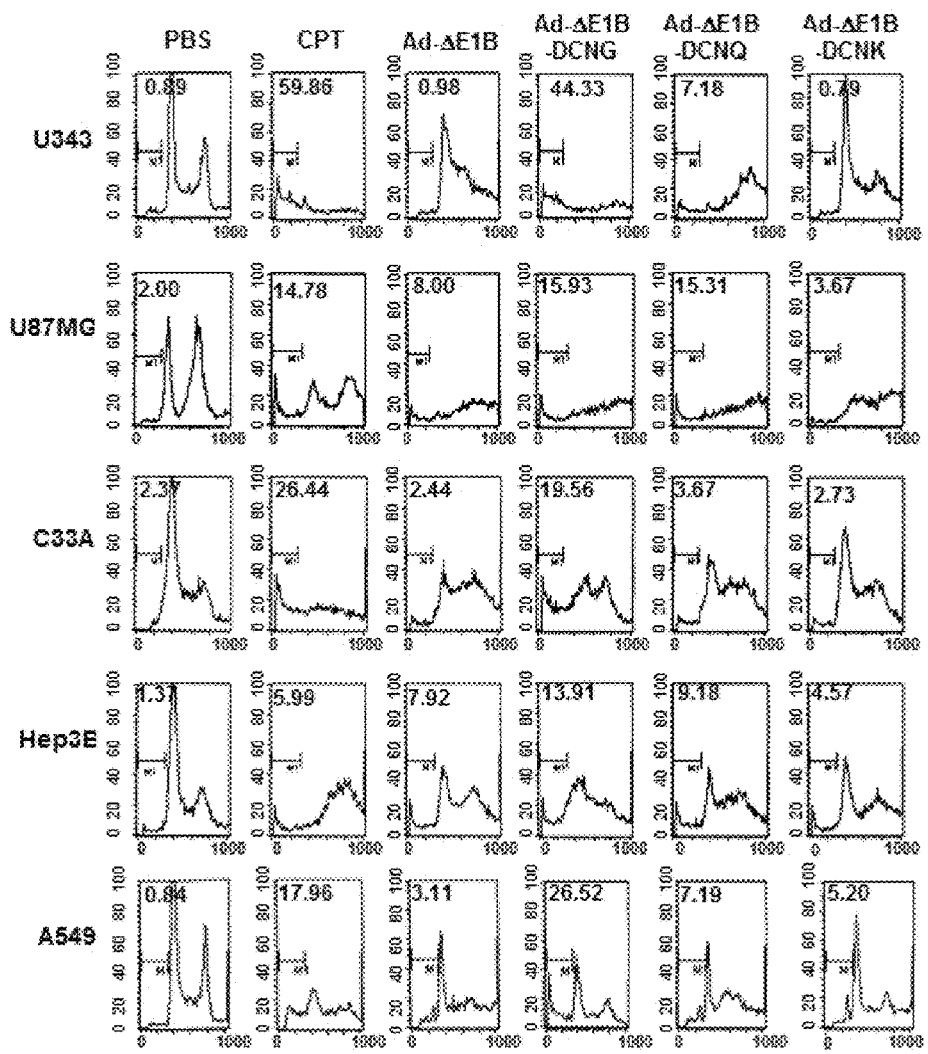
FIGS. 8a and 8b show the results of the flow cytometry analysis for PI staining verifying the apoptosis-inducing potency of the present adenoviruses in human tumor cell lines (U343, U87MG, C33A, Hep3B and A549).

The replication incompetent adenovirus, dl-LacZ-DCNG at high titer was revealed to induce the death of cells that were detached from the bottom of culture plates as shown in Result 2. Therefore, we examined whether decorin expression is responsible for cytotoxic effect. First, to determine whether decorin induces apoptosis, flow cytometric assay was carried out after PI staining for analyzing an increase rate of subG$_1$ cell population containing randomly fragmented DNAs due to apoptosis. Various human tumor cell lines were infected with Ad-ΔE1B, Ad-ΔE1B-DCNG, Ad-ΔE1B-DCNQ and Ad-ΔE1B-DCNK adenoviruses and harvested after 48-96 hr post-infection for measuring an increase in subG$_1$ cell population. CPT was used as a positive control for the induction of apoptosis. A549 cells infected with Ad-ΔE1B showed about 3.11% of subG$_1$ cell population and those infected with Ad-ΔE1B-DCNG showed about 26.52% of subG$_1$ cell population. Such increased subG$_1$ cell population by adenoviral infection was also observed in other cell lines (U343, U87MG, C33A and Hep3B) (FIG. 8a and Table 1). Moreover, subG$_1$ cell population in cells infected with Ad-ΔE1B-DCNQ and Ad-ΔE1B-DCNK was decreased compared to Ad-ΔE1B-DCNG; the increase in subG$_1$ cell population was less upon decreasing the binding affinity of decorin to collagen.

Figure 8B:
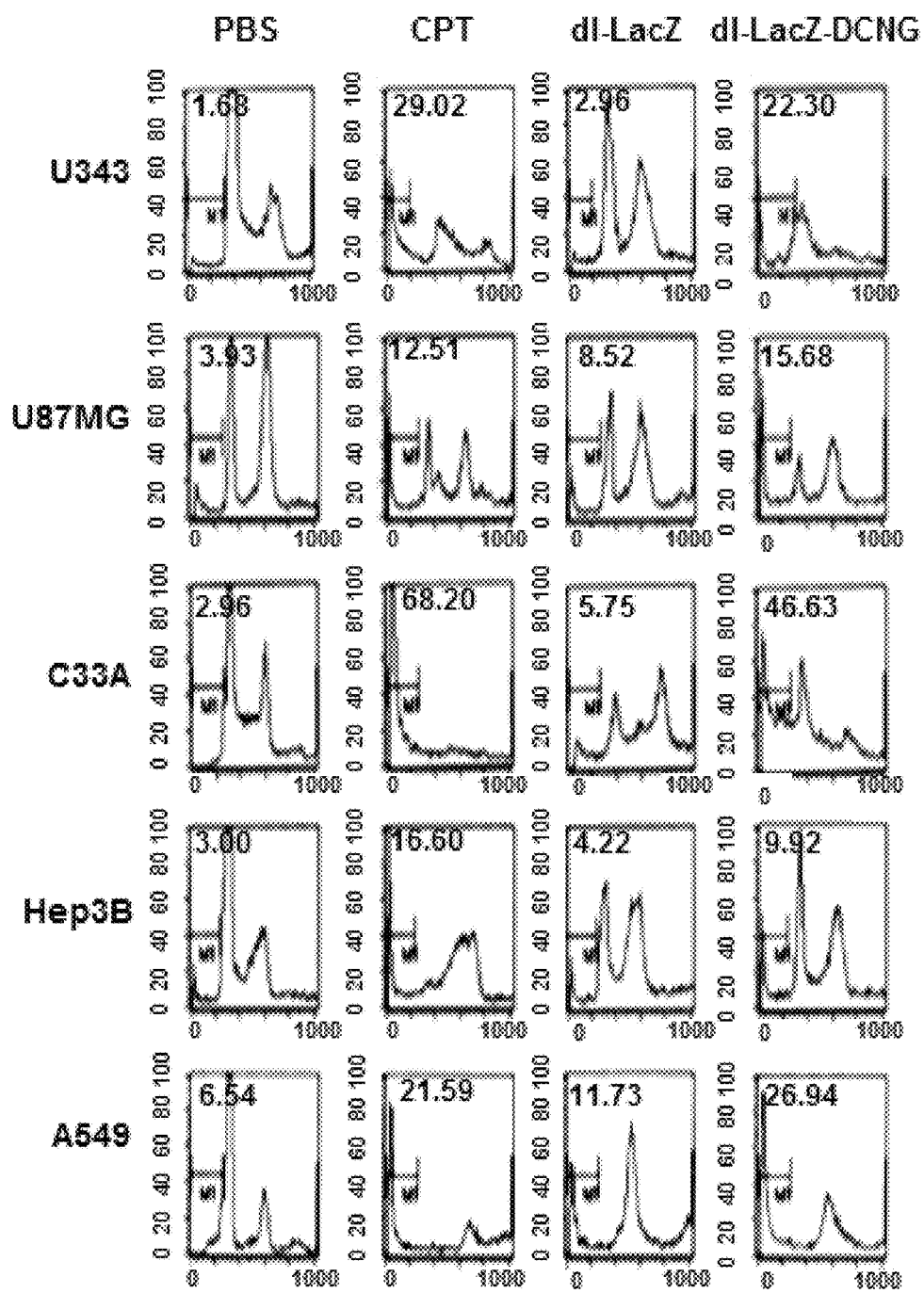

A representative of human tumor cell lines was infected with replication-incompetent adenoviruses, dl-LacZ or dl-LacZ-DCNG adenovirus and harvested for measuring the increase in subG$_1$ cell population. As results observed in oncolytic adenoviruses described above, dl-LacZ-DCNG gave rise to larger subG$_1$ cell population than dl-LacZ (FIG. 8b and Table 2).

TABLE 1

| Tumor cell lines | subG1 cell population (%) | | | |
|---|---|---|---|---|
| | PBS | CPT | Ad-ΔE1B | Ad-ΔEIB-DCNG |
| U343 | 0.89 | 59.86 | 0.98 | 44.33 |
| U87MG | 2.00 | 14.78 | 8.00 | 15.93 |
| C33A | 2.37 | 26.44 | 2.44 | 19.56 |
| Hep3B | 1.37 | 5.99 | 7.92 | 13.91 |
| A549 | 0.84 | 17.96 | 3.11 | 26.52 |

TABLE 2

| Tumor cell lines | subG1 cell population (%) | | | |
|---|---|---|---|---|
| | PBS | CPT | dl-LacZ | dl-LacZ-DCNG |
| U343 | 1.68 | 29.02 | 2.96 | 22.30 |
| U87MG | 3.93 | 12.51 | 8.52 | 15.68 |
| C33A | 2.96 | 68.20 | 5.75 | 46.63 |
| Hep3B | 3.00 | 16.60 | 4.22 | 9.92 |
| A549 | 6.54 | 21.59 | 11.73 | 26.94 |

Figure 9A:
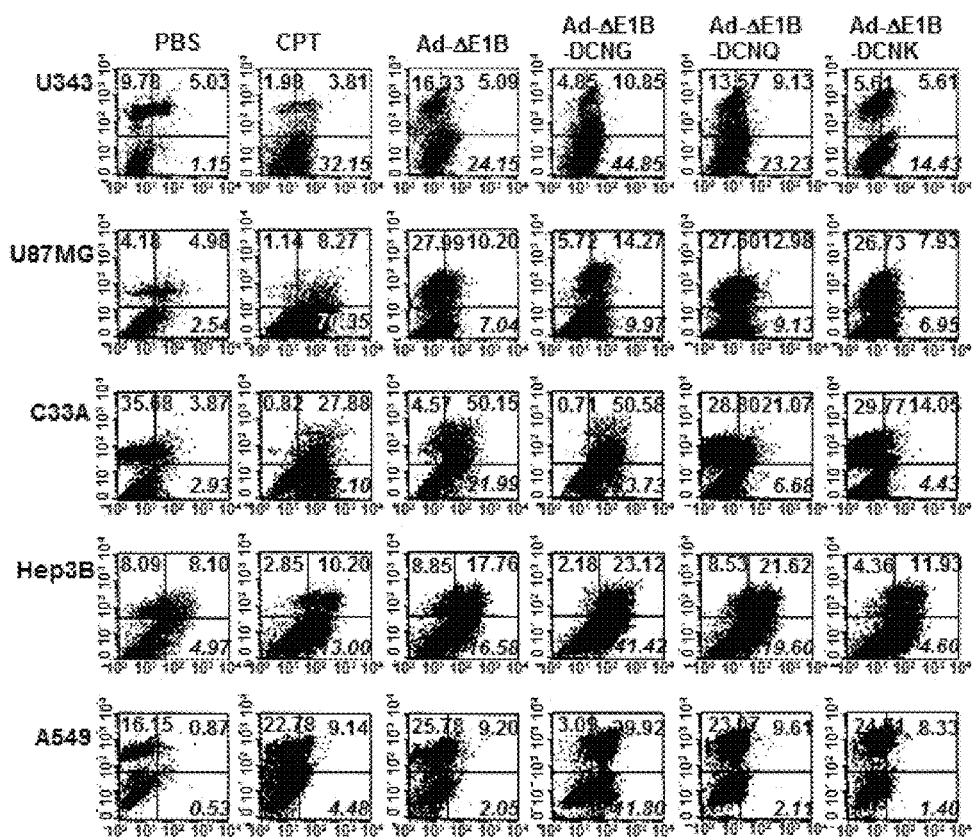
FIGS. 9a and 9b show the results of Annexin-V-PI double staining and flow cytometry analysis verifying the ability of the recombinant adenoviruses to induce apoptosis and necrosis in human tumor cell lines (U343, U87MG, C33A, Hep3B and A549).

Further, to accurately examine the effect of decorin expression on cell killing potency, the progress of apoptosis induced by oncolytic adenoviruses was assessed by Annexin V-FITC and PI dual staining. Annexin V-FITC is used to detect the translocation of phosphatidylserin (PS) to the external membrane leaflet as an early marker for apoptosis, and PI is used to identify necrosis by binding to nuclear chromatin as a late marker for apoptosis. Therefore, Annexin V-FITC$^-$/PI$^-$, Annexin V-FITC$^+$/PI$^-$ and PI$^+$ represent healthy, apoptotic and necrotic cells, respectively. Of the CPT-treated U343 cells, 32.15% (Annexin V-FITC$^+$/PI$^-$) of the cells were apoptotic, while the cells infected with Ad-ΔE1B and Ad-ΔE1B-DCNG showed 24.15% and 44.85% apoptotic rate, respectively, indicating that Ad-ΔE1B-DCNG adenovirus induces enhanced apoptosis rate compared to Ad-ΔE1B (FIG. 9a). For other cell lines including U87MG, C33A, Hep3B and A549, the decorin-expressing adenovirus showed much higher apoptosis rate than Ad-ΔE1B adenovirus. In addition, the total of apoptosis and necrosis (Annexin V-FITC$^+$/PI$^-$ and PI$^+$) reflecting the entire cell death was elucidated to be much higher for Ad-ΔE1B-DCNG than Ad-ΔE1B. Collectively, these results urge us to reason that Ad-ΔE1B-DCNG adenovirus elicits much higher rate of apoptosis than Ad-ΔE1B, so that the cell death occurs more frequently by Ad-ΔE1B-DCNG than Ad-ΔE1B. Moreover, we found that the apoptotic rate by Ad-ΔE1B-DCNQ and Ad-ΔE1B-DCNK was decreased compared to that by ΔE1B-DCNG; the apoptotic rate was decreased upon decreasing the binding affinity of decorin to collagen.

Figure 9B:
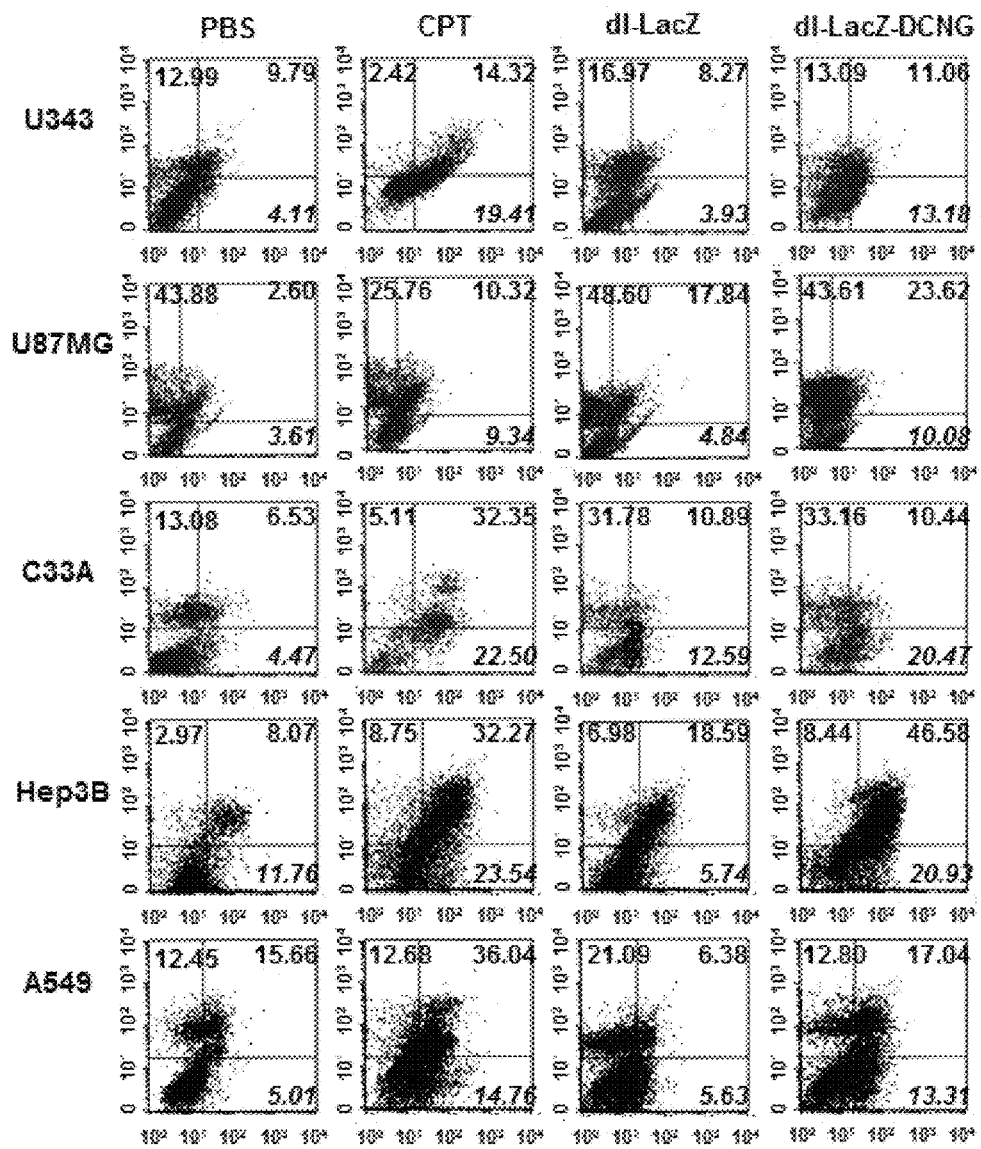

To examine the apoptotic rate induced by replication-incompetent decorin-expressing adenoviruses, various cells including U343, U87MG, C33A, Hep3B and A549 were treated with PBS, CPT, dl-LacZ or dl-LacZ-DCNG and the progress of apoptosis was then assessed by Annexin V-FITC and PI dual staining. As shown in FIG. 9b, of the CPT-treated U343 cells, 19.41% (Annexin V-FITC$^+$/PI$^-$) of the cells were apoptotic, while the cells infected with dl-LacZ and dl-LacZ-DCNG showed 3.93% and 13.18% apoptotic rate, respectively, indicating that dl-LacZ-DCNG adenovirus induces enhanced apoptosis rate compared to dl-LacZ. For other cell lines including U87MG, C33A, Hep3B and A549, the decorin-expressing dl-LacZ-DCNG adenovirus showed much higher apoptosis rate than the dl-LacZ adenovirus. Taken together, it could be recognized that replication-incompetent decorin-expressing adenoviruses as well as oncolytic decorin-expressing adenoviruses could induce apoptosis at much higher rate.

TUNNEL assay was performed for identifying DNA fragmentation as a characteristic of early apoptosis. It was shown in FIG. 10a and Table 3 that almost all the cells treated with CPT as a positive control were stained to dark brown, indicating the occurrence of active apoptosis. 32.5±12.5% of Ad-ΔE1B-infected U343 cells appeared light brown and 69.7±5.40% of Ad-ΔE1B-DCNG-infected cells dark brown, demonstrating the higher potency of Ad-ΔE1B-DCNG to induce apoptosis than Ad-ΔE1B (Table 3). Such increased apoptosis upon decorin expression was also found in other tumor cell lines (U87MG, C33A, Hep3B and A549). We found that the frequency of DNA fragmentation induced by Ad-ΔE1B-DCNQ and Ad-ΔE1B-DCNK was less compared to that by Ad-ΔE1B-DCNG; the frequency of DNA fragmentation was decreased as the binding affinity of decorin to collagen was decreased. Since various effects exerted by decorin expression were sufficiently analyzed and assessed in terms of the binding affinity to collagen, adenoviruses expressing the wild type decorin having the highest binding affinity to collagen were used for in vivo or in vitro efficacy tests.

TABLE 3

| Tumor cell line | Proportion of apoptotic cells (%) | | | |
| --- | --- | --- | --- | --- |
| | PBS | CPT | Ad-ΔE1B | Ad-ΔE1B-DCNG |
| U343 | 10.5 ± 5.83 | 53.5 ± 7.45 | 32.5 ± 12.5 | 69.7 ± 5.40 |
| U87MG | 2.5 ± 1.11 | 83.0 ± 29.29 | 16.5 ± 5.21 | 77.0 ± 17.98 |
| C33A | 5.65 ± 3.29 | 60.1 ± 25.91 | 45.2 ± 7.61 | 79.8 ± 20.51 |
| Hep3B | 1.65 ± 0.61 | 71.2 ± 15.73 | 38.5 ± 2.65 | 69.7 ± 15.64 |
| A549 | 3.5 ± 0.83 | 37.5 ± 5.35 | 34.8 ± 11.3 | 75.21 ± 1.22 |

| Tumor cell line | Proportion of apoptotic cells (%) | | | |
| --- | --- | --- | --- | --- |
| | PBS | CPT | dl-LacZ | dl-LacZ-DCNG |
| U343 | 1.54 ± 2.98 | 74.67 ± 12.38 | 15.07 ± 7.43 | 61.82 ± 15.20 |
| U87MG | 1.94 ± 1.58 | 40.00 ± 13.17 | 15.00 ± 2.44 | 44.44 ± 7.24 |
| C33A | 3.61 ± 2.45 | 70.51 ± 15.90 | 18.56 ± 9.99 | 54.74 ± 13.29 |
| Hep3B | 3.33 ± 1.56 | 75.86 ± 3.11 | 23.58 ± 9.23 | 45.28 ± 7.34 |
| A549 | 3.00 ± 2.21 | 69.80 ± 8.38 | 7.84 ± 2.42 | 52.08 ± 13.66 |

Figure 10A:
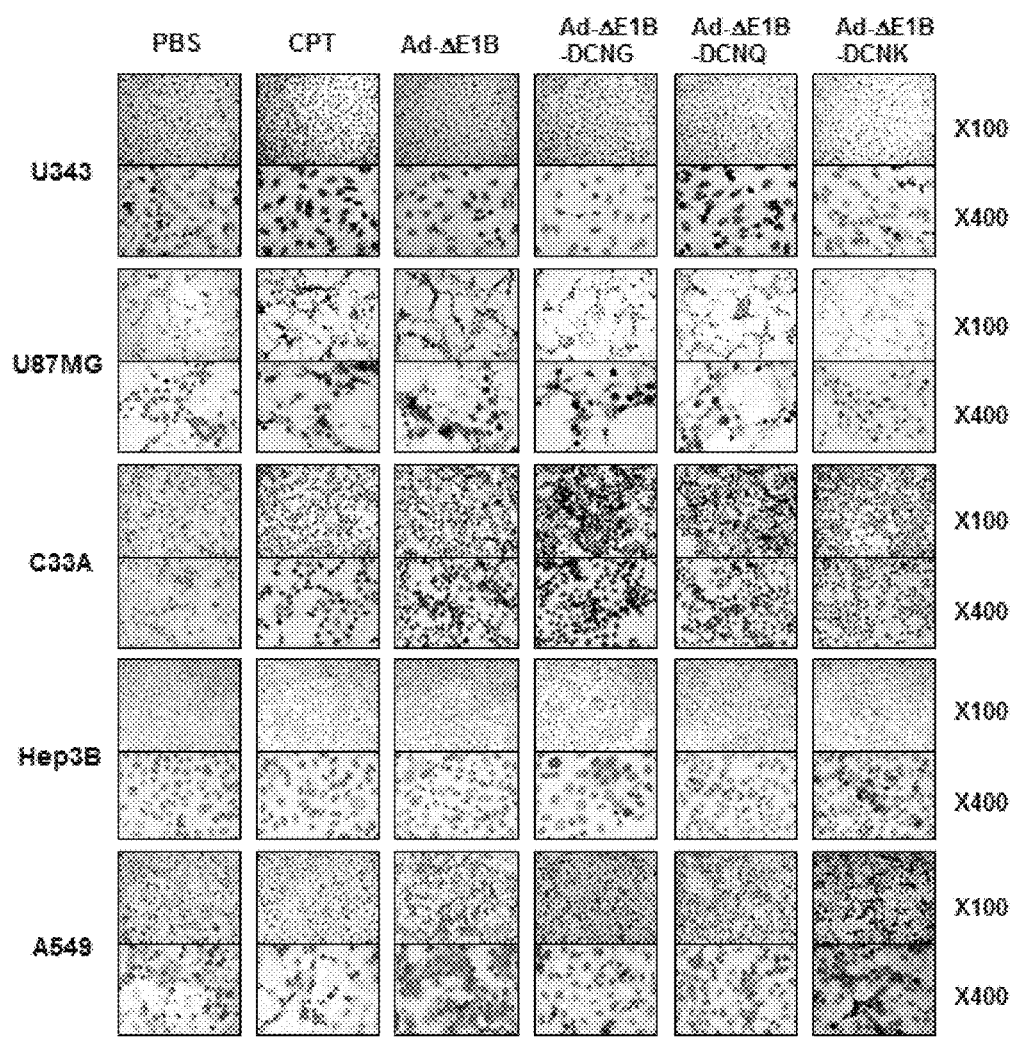
FIGS. 10a and 10b represent the results of TUNEL assay demonstrating the ability of the recombinant adenoviruses to induce apoptosis into human tumor cell lines (U343, U87MG, C33A, Hep3B and A549).
Figure 10B:
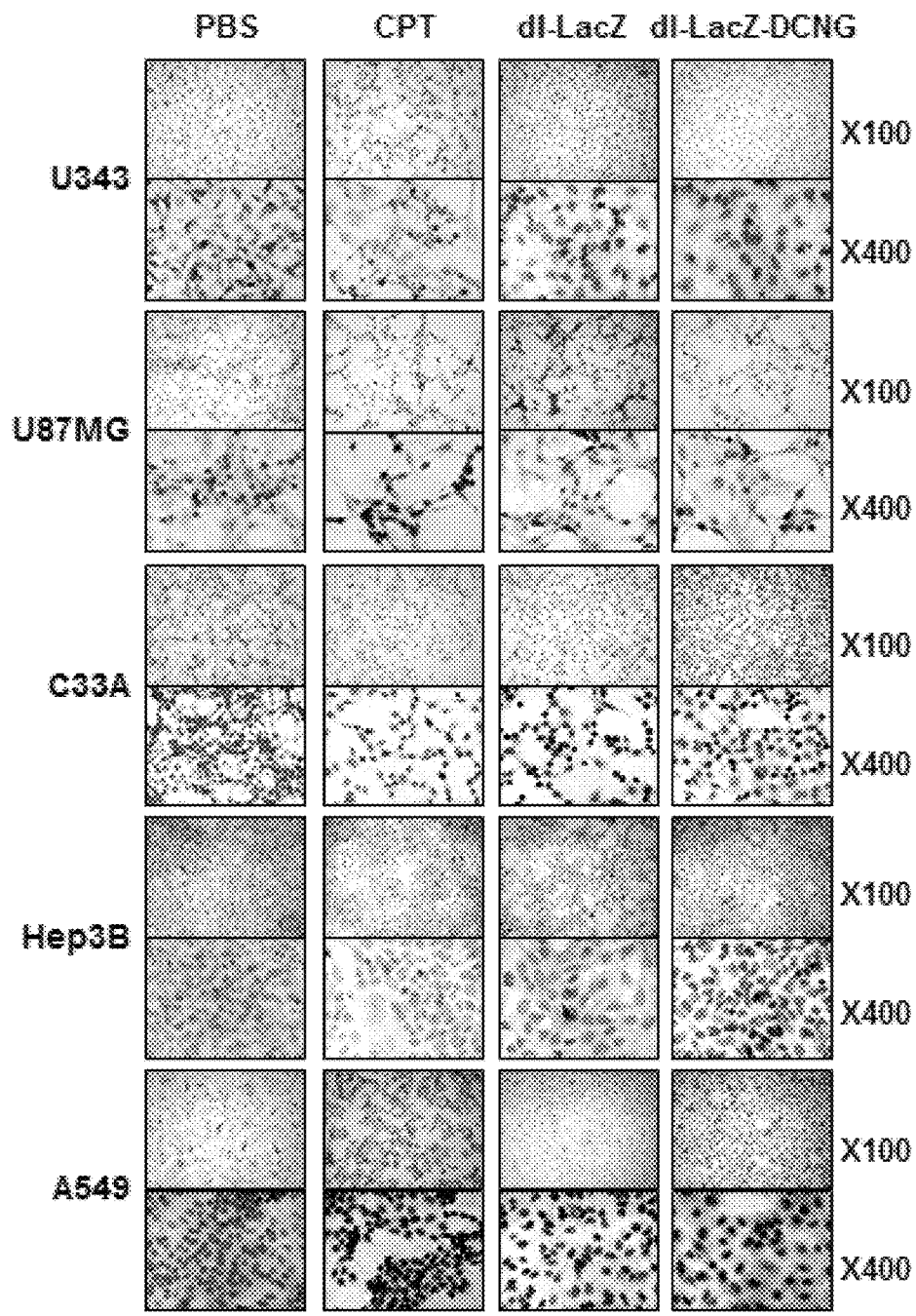

A representative of human tumor cell lines was infected with replication-incompetent adenovirus (dl-LacZ or dl-LacZ-DCNG) or tumor-specific oncolytic adenovirus (Ad-ΔE1B or Ad-ΔE1B-DCNG), and harvested 48-96 hr after infection for TUNNEL analysis. As results obtained from oncolytic adenoviruses, the decorin-expressing dl-LacZ-DCNG and Ad-ΔE1B-DCNG adenoviruses exhibited much higher apoptosis rate than the dl-LacZ adenovirus (FIG. 10a, FIG. 10b, Table 3).

Figure 11A:
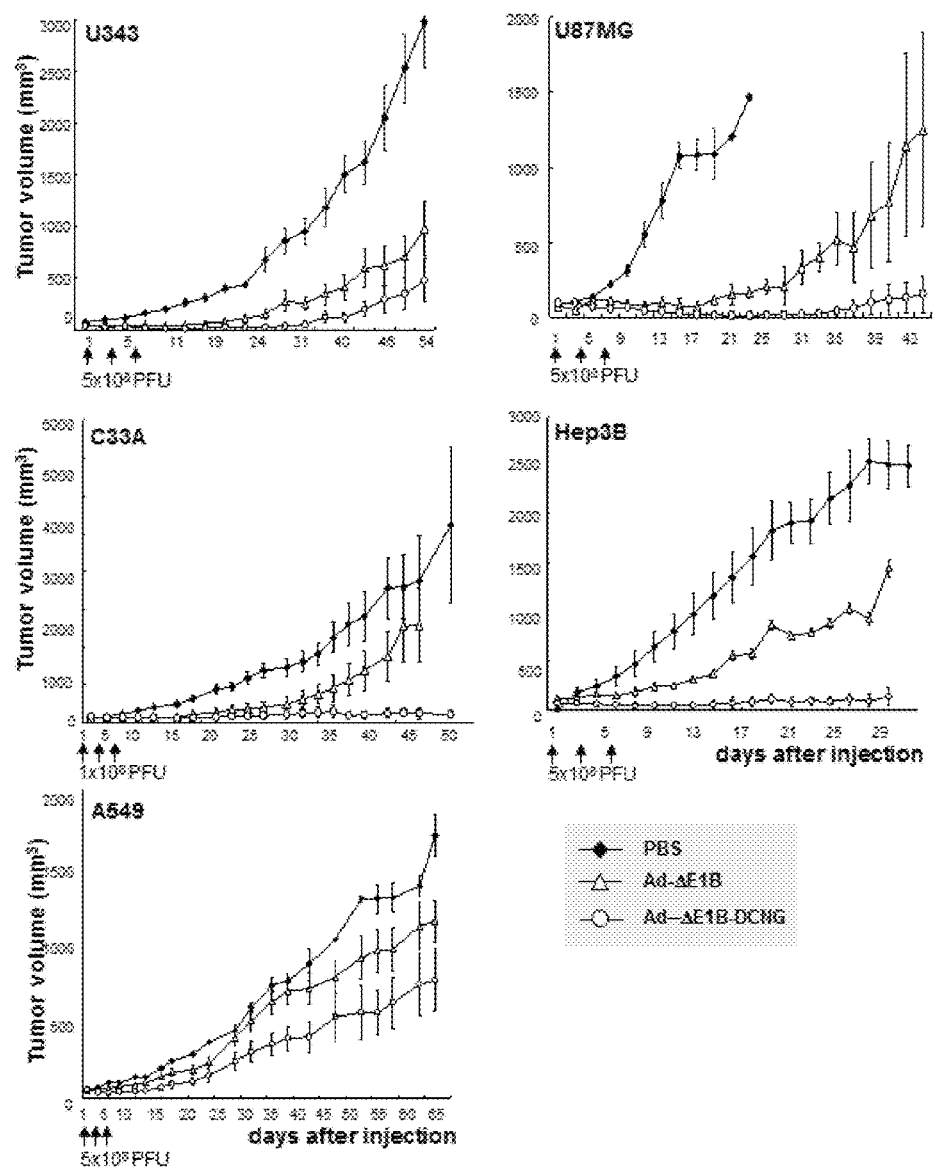
FIGS. 11a and 11b are the graphs representing the change in the tumor size (FIG. 11a) and the survival rate (FIG. 11b) of tumor (U343, U87MG, C33A, Hep3B and A549)-bearing mice injected with the tumor-specific oncolytic Ad-ΔE1B-DCNG adenovirus of this invention.

8. Evaluation on Anti-Tumor Effect of Decorin-Expressing Oncolytic Adenovirus In Vivo To investigate in vivo anti-tumor effect of decorin-expressing Ad-ΔE1B-DCNG, tumors xenografts formed in nude mice were infected three times every other day with Ad-ΔE1B or Ad-ΔE1B-DCNG at $1\times10^8$-$5\times10^8$ PFU and the growth pattern of tumors was observed. For human brain tumor U87MG, the negative control PBS resulted in the considerable growth of tumor to 1089.22 mm³, whereas Ad-ΔE1B and Ad-ΔE1B-DCNG led to the significant suppression of tumor growth to 115.70 mm³ and 11.87 mm³, respectively (FIG. 11a). In other words, Ad-ΔE1B and Ad-ΔE1B-DCNG adenoviruses exhibited prominent in vivo anti-tumor effect with referring to results from PBS.

Figure 11B:
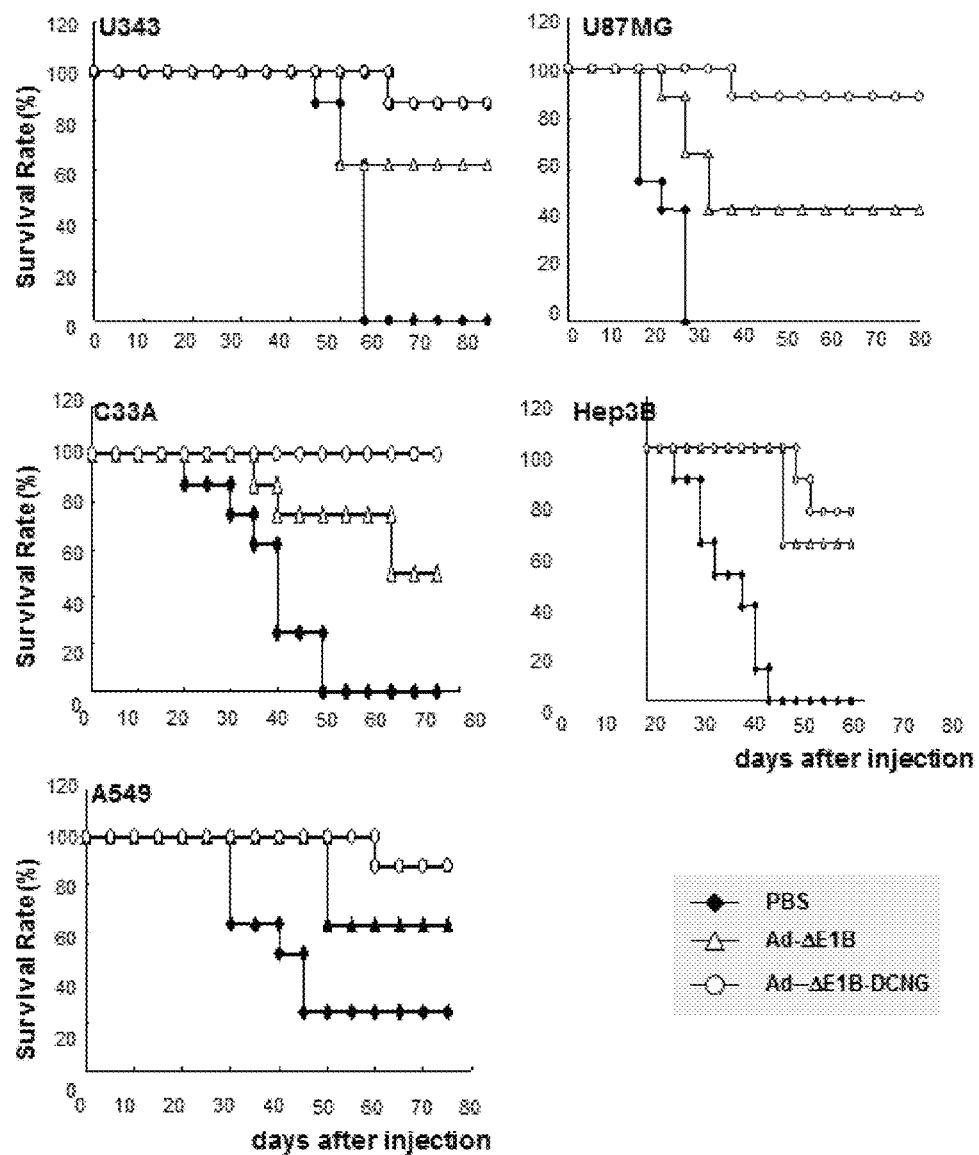
Figure 12A:
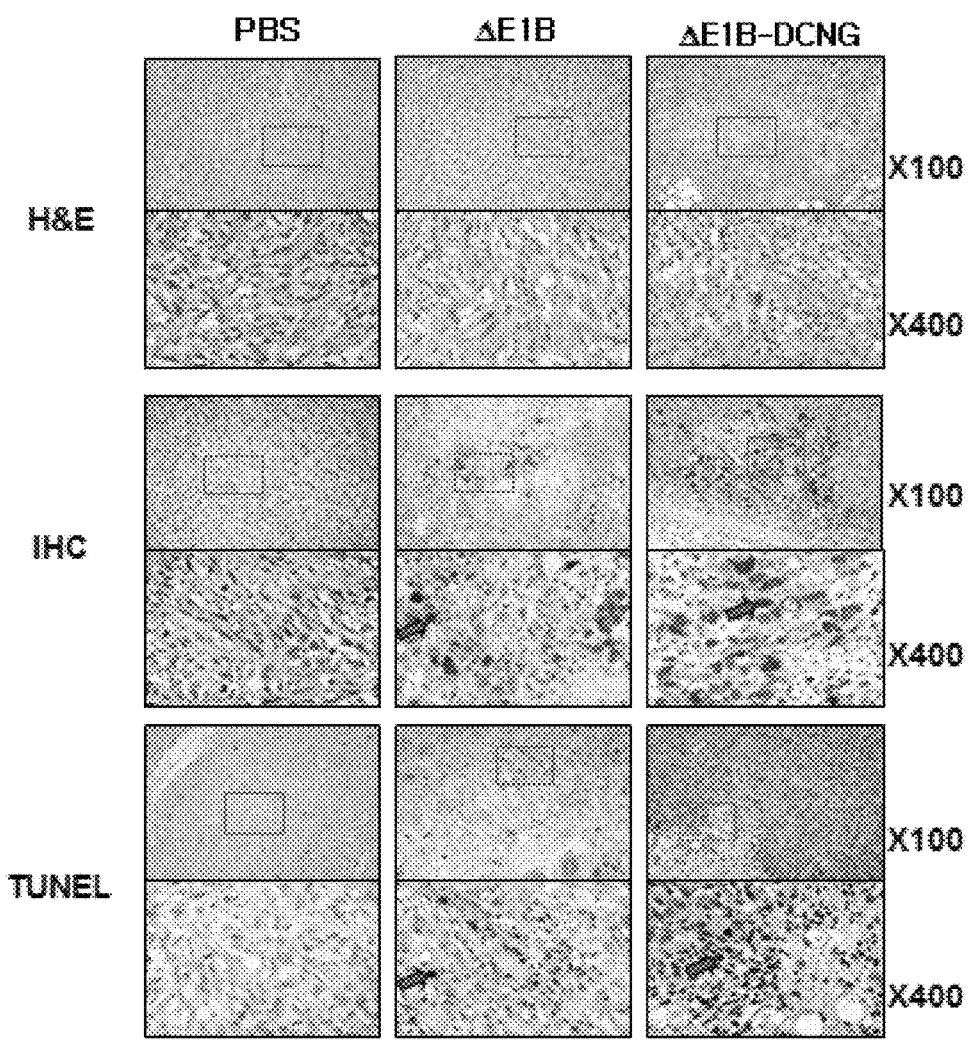
FIGS. 12a, 12b, 12c, 12d and 12e show the results of H&E, IHC (immunohistochemical) staining and TUNEL analysis for U343 (FIG. 12a), U87MG (FIG. 12b), C33A (FIG. 12c), Hep3B (FIG. 12d) and A549 (FIG. 12e) in tumor-bearing mice infected with the tumor specific oncolytic adenovirus, Ad-ΔE1B-DCNG of this invention.
Figure 12B:
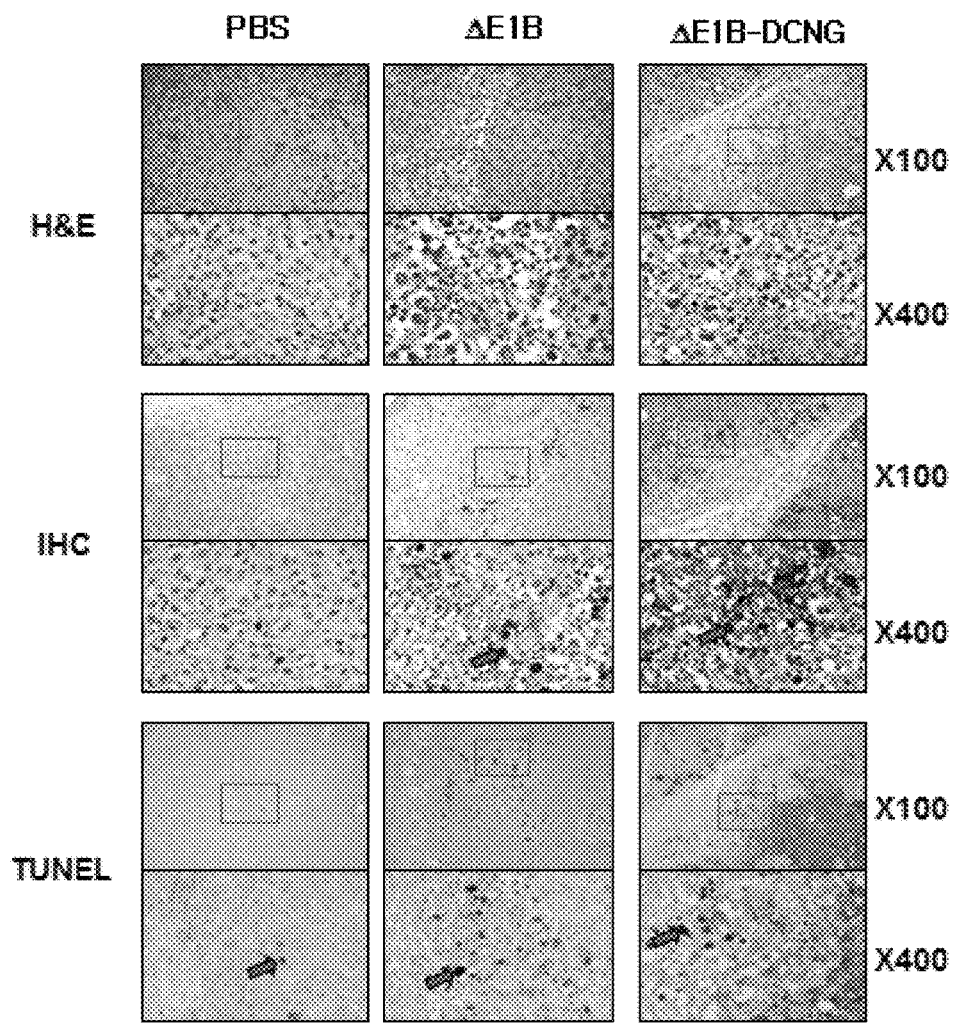
Figure 12C:
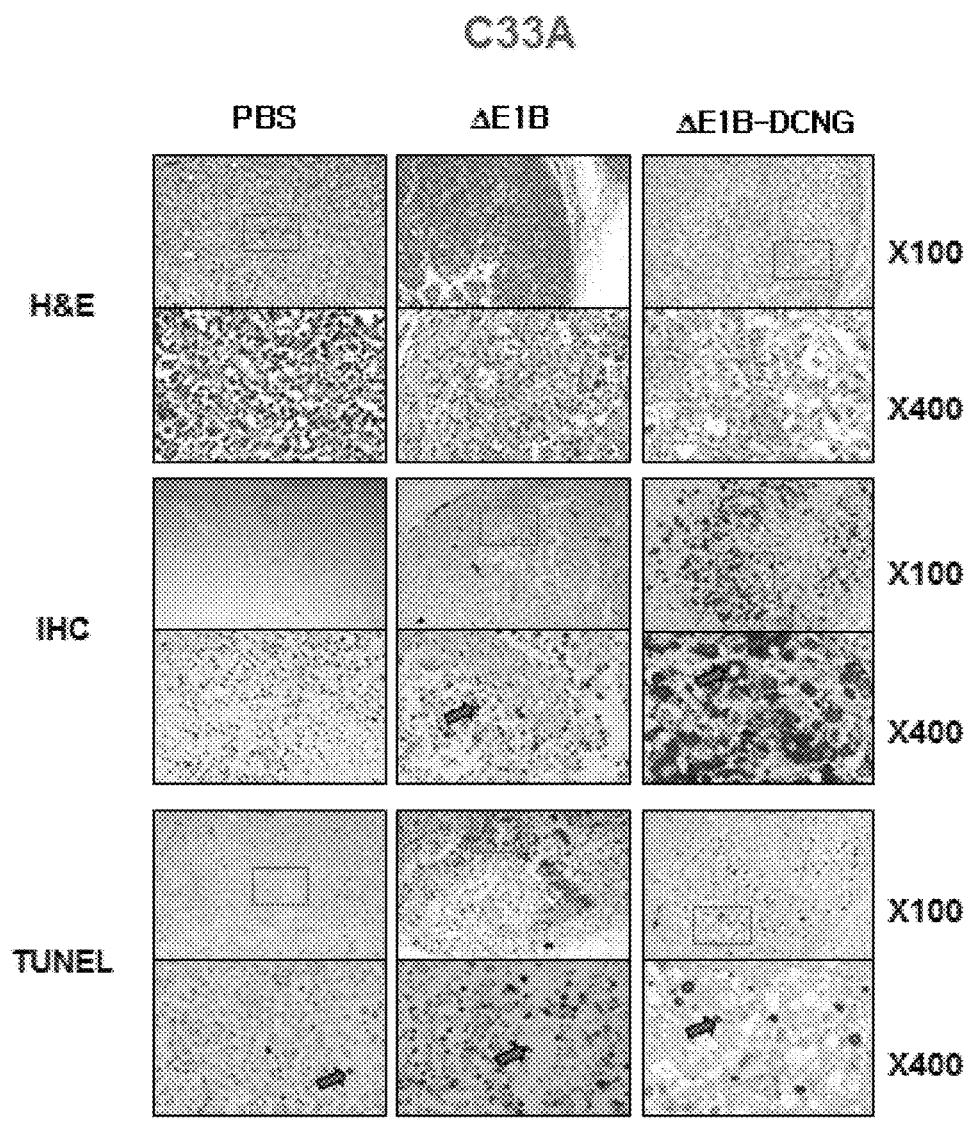
Figure 12D:
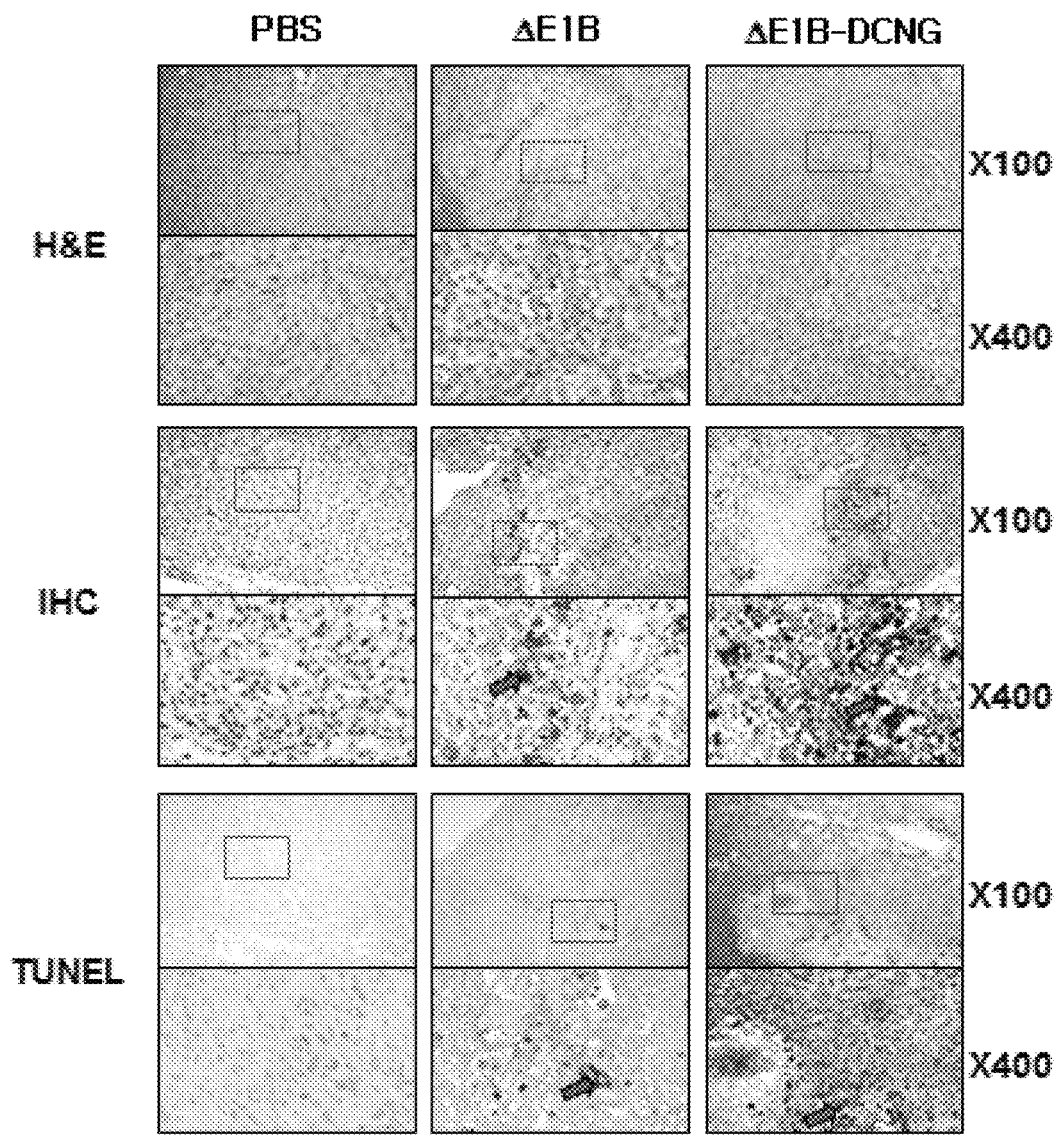
Figure 12E:
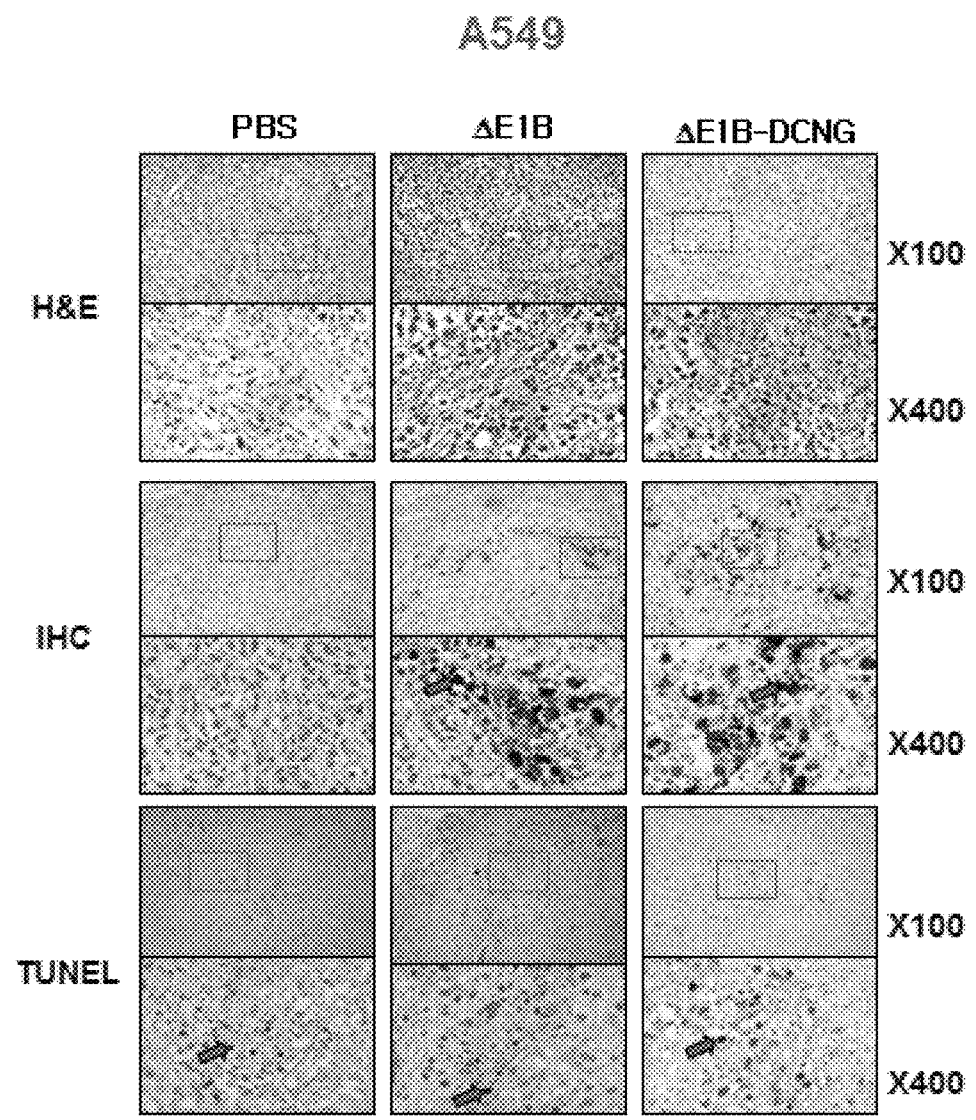

After 25 days post-treatment, all of 9 mice treated with PBS were dead (FIG. 1b). After 33 days post-infection, Ad-ΔE1B and Ad-ΔE1B-DCNG adenoviruses led to the tumor volume of 399.68 mm³ and 23.38 mm³, respectively, reasoning that the decorin-expressing adenovirus has stronger anti-tumor potency than Ad-ΔE1B. Surprisingly, Ad-ΔE1B-DCNG adenovirus completely eradicated tumor in 4 mice of 7 mice at day 19 post-viral infection and wiped out tumor in 6 mice at day 41 post-infection. Also, the regrowth of tumor treated with Ad-ΔE1B-DCNG was not observed even after 60 days post-infection (FIG. 11b). To examine whether such excellent anti-tumor effect of Ad-ΔE1B-DCNG is also true in other human tumor cell lines, the analysis of anti-tumor effects was carried out for C33A, A549, Hep3B and U343 xenografts. The groups administered with tumor-specific oncolytic Ad-ΔE1B or Ad-ΔE1B-DCNG adenovirus showed more remarkable anti-tumor effect than those treated with PBS, as shown in FIG. 11a. In addition, tumors treated with Ad-ΔE1B-DCNG were more largely decreased in volume than those treated with Ad-ΔE1B, demonstrating the contribution of decorin expression to excellent in vivo anti-tumor effect.

The survival rate of tumor-bearing mice was examined for the decorin-expressing adenovirus treatment. For C33A tumor bearing mice, 80 days after the beginning of the treatment, 100% of the animals treated with Ad-ΔE1B-DCNG) were still viable, whereas only 50% of Ad-ΔE1B-treated mice were viable (death of mice; tumor volume>2000 mm for C33A) in the same time period (FIG. 11b). Ad-ΔE1B-DCNG was treated at $1\times10^8$ PFU for C33A xenograft model and at $5\times10^8$ PFU for U343, U87MG, Hep3B and A549 xenograft models. Such increased survival rate by Ad-ΔE1B-DCNG was also measured in U343, U87MG, Hep3B and A549 xenograft models. These results demonstrate that Ad-ΔE1B-DCNG can confer significant survival benefits and tumor reduction in vivo.

9. Change of Tumor Characteristics Induced by Decorin-Expressing Replication-Competent Adenovirus Various human tumor cell lines (U343, U87MG, C33A, Hep3B and A549) formed in the abdomen of nude mice was infected three times with Ad-ΔE1B and Ad-ΔE1B-DCNG. Following 3 days of injection, the tumor tissues were extracted and stained with hematoxylin and eosin for histological characterization. As shown in FIGS. 12a-12e, necrotic lesions in Ad-ΔE1B-DCNG-treated tumors were mainly found on the periphery of tumor mass, whereas those in Ad-ΔE1B-treated tumors were barely detectable, if any, found at the center of tumor mass. Viral persistence and distribution within the tumor mass was then verified by immunohistochemistry using antibodies specific to adenoviral hexon protein. As shown in FIGS. 12a-12e, Ad-ΔE1B-DCNG adenovirus was detected mainly on the periphery of tumor that underwent necrosis. TUNNEL assay revealed that apoptosis occurred actively in the same region as necrosis. In contrast, Ad-ΔE1B induced necrosis at the center of tumor, if detectable.

Summarizing, it could be recognized that Ad-ΔE1B-DCNG adenovirus replicates actively in the viral injection site and spreads widely, contributing to the induction of apoptosis and necrosis.

Figure 13:
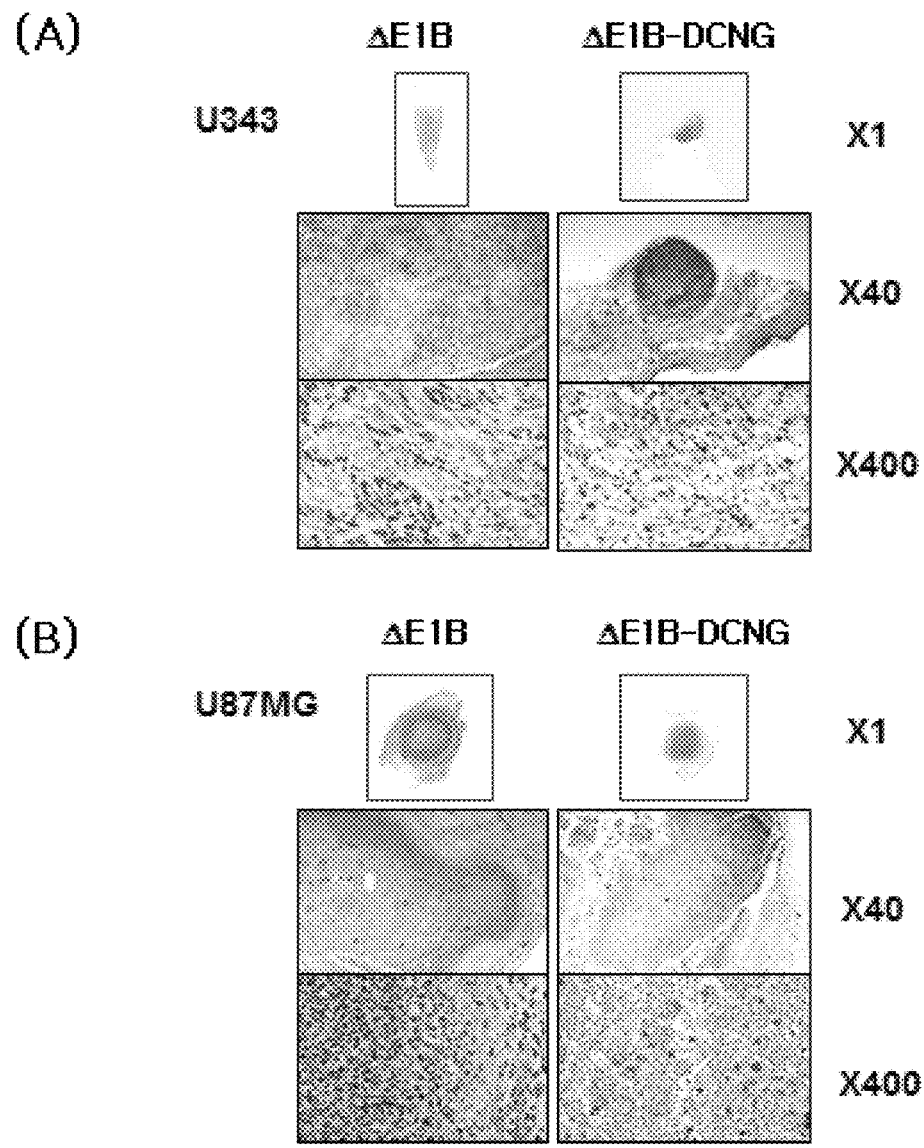
FIG. 13 represents the results of Mansson's trichrome staining demonstrating collagen distribution within extracellular matrix of U343 (panel A) and U87MG (panel B) tumors in tumor-bearing mice injected with the tumor specific oncolytic adenovirus of this invention (Ad-ΔE1B or Ad-ΔE1B-DCNG).

10. Investigation of Collagen Distribution in Tumor Mass Using Masson's Trichrome Staining Human brain tumor cell line U343 formed in nude mice was injected three times with Ad-ΔE1B or Ad-ΔE1B-DCNG. Following 3 days of injection, the tumor tissues were extracted and stained with Masson's trichrome to analyze the distribution of collagen (stained blue color), major component of extracellular matrix, trichrome stain). U343 tumor mass treated with Ad-ΔE1B was frequently observed to be stained in blue color within its inner portion; however, that treated with Ad-ΔE1B-DCNG showed no blue staining within its inner portion. Instead, collagen in the form of capsule was observed in normal tissues surrounding tumors (FIG. 13, panel A). These results suggest that the oncolytic Ad-ΔE1B-DCNG adenovirus expresses decorin in the tumor-specific manner and then dramatically reduces the collagen content within the tumor mass with no influence on the collagen content within surrounding normal tissues.

For U87MG xenograft model, the tumor mass injected with Ad-ΔE1B-DCNG showed little or no blue-stained region due to very low level of collagen as that injected with Ad-ΔE1B (FIG. 13, panel B). Accordingly, it would be appreciated that in the case that the level of collagen is low in tumor tissues, the expression of decorin is unlikely to affect collagen content.

11. Examination for Expression Pattern of MMP by Zymography

Figure 14:
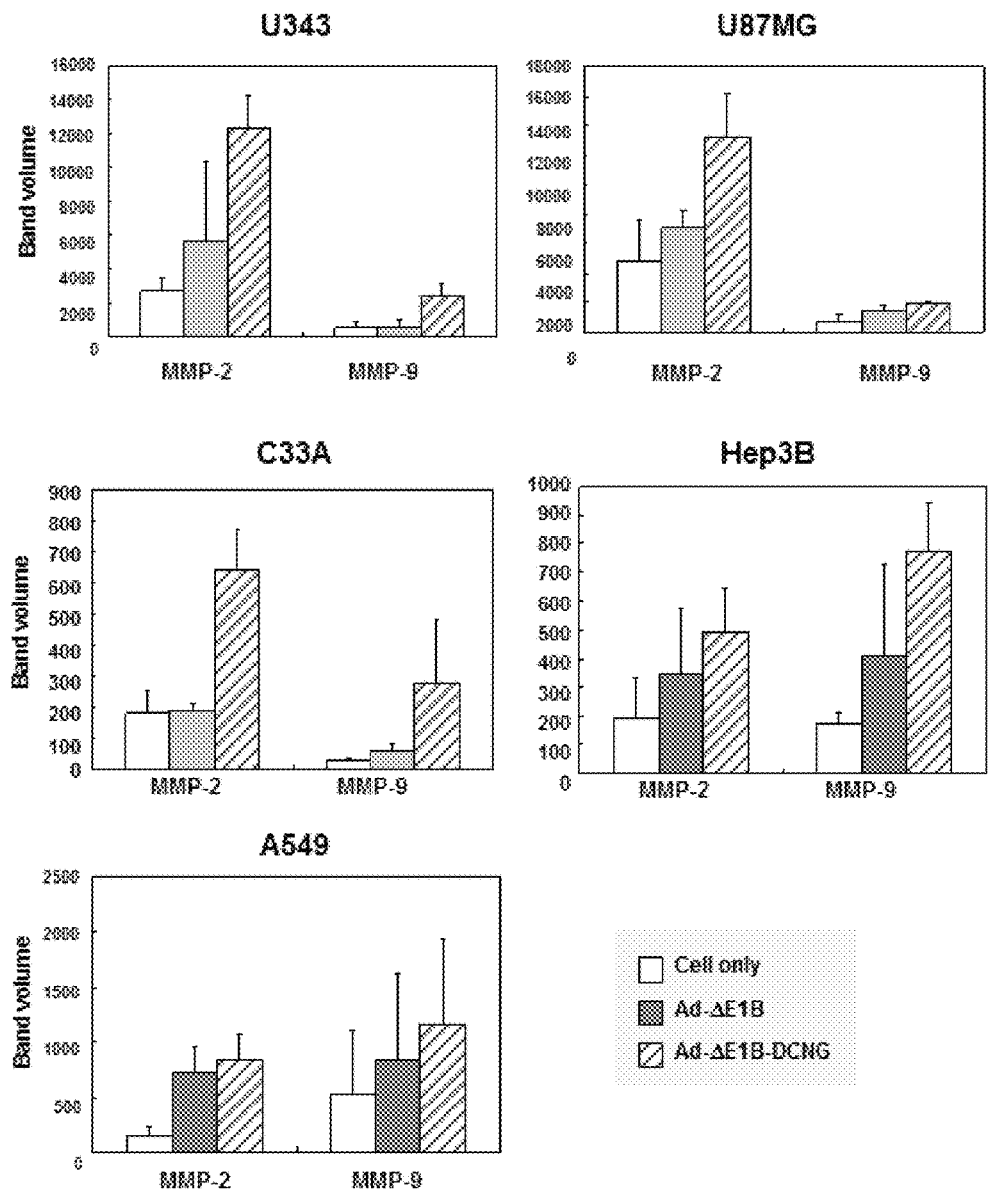
FIG. 14 numerically represents the results of gelatin zymography electrophoresis which shows the expression pattern of MMP in human tumor cell lines U343, U87MG, C33A, Hep3B and A549 infected with either Ad-ΔE1B or Ad-ΔE1B-DCNG.

To examine whether the decrease in extracellular matrix is induced by MMP, the activities of MMP-2 and MMP-9 were verified by zymography (FIG. 14). Various human tumor cell lines (U343, U87MG, C33A, Hep3B and A549) were infected with Ad-ΔE1B or Ad-ΔE1B-DCNG adenovirus at various titers. As results, the activities of MMP-2 and MMP-9 were enormously increased when infected with the Ad-ΔE1B-DCNG adenovirus compared to PBS and Ad-ΔE1B as a control. These elevated activities of MMP-2 and MMP-9 were found at the similar extent in all U343, U87MG, C33A, Hep3B and A549 cell lines. It could be therefore understood that the activities of MMP-2 and MMP-9 can be increased by the decorin expression of adenoviruses.

12. Inhibition of Tumor Metastasis by Decorin-Expressing Oncolytic Adenovirus

Figure 15:
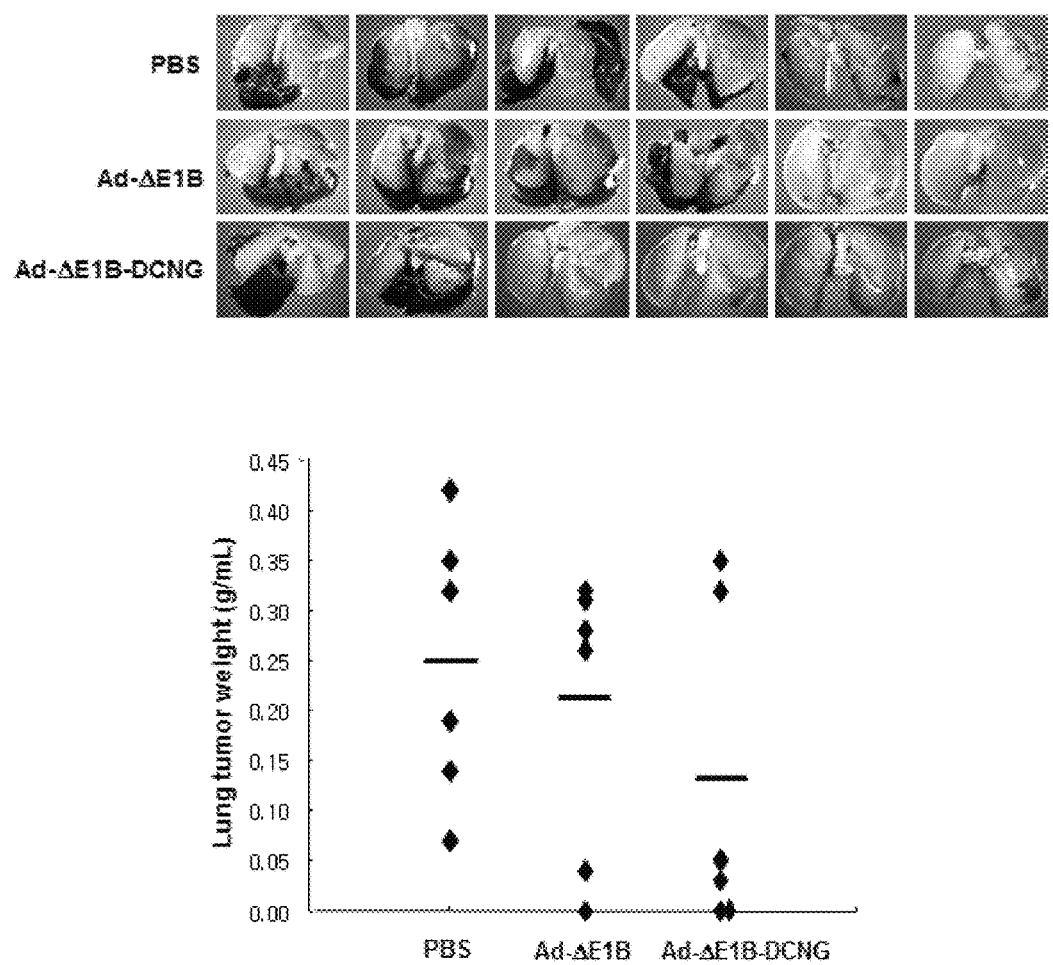
FIG. 15 represents the results of the effect of decorin expression on tumor metastasis using B16BL6 spontaneous tumor metastatic model (upper panel) and the weight of metastatic lung tumor (lower panel).

It is generally known that decorin reacts with extracellular matrix components to promote the expressions of MMP-1 and MMP-2, thereby degrading extracellular matrix. The change in metastatic potential over decorin expression was examined using spontaneous metastasis model. B16BL6 cells ($2 \times 10^5$/mouse) were administered subcutaneously into the right hind foot pad of C57BL/6 mice and, once the tumor volume reached to a volume of 100-200 mm³, PBS, Ad-ΔE1B or Ad-ΔE1B-DCNG was injected directly into the tumor three times every other day. On day 5 after last injection, the primary tumors were surgically removed by amputating below knee under mild anesthesia. On day 20 following primary tumor removal, the weight of metastatic tumor lesions in the lungs of the mice was assessed. As shown in FIG. 15, the average tumor burden in the lung from mice treated with Ad-ΔE1B and Ad-ΔE1B-DCNG was 200±140 mg and 130±160 mg, respectively, showing much smaller pattern, compared to PBS-treated control group (250±140 mg). Moreover, Ad-ΔE1B and Ad-ΔE1B-DCNG inhibited the formation of metastatic lesions completely in 1 and 2 out of 7 treated mice, respectively, although all of 7 mice treated with PBS showed severe metastasis of lung cancer. These data indicate that the decorin expression in primary tumor site can suppress the formation of metastatic lesions at distal sites.

Figure 16:
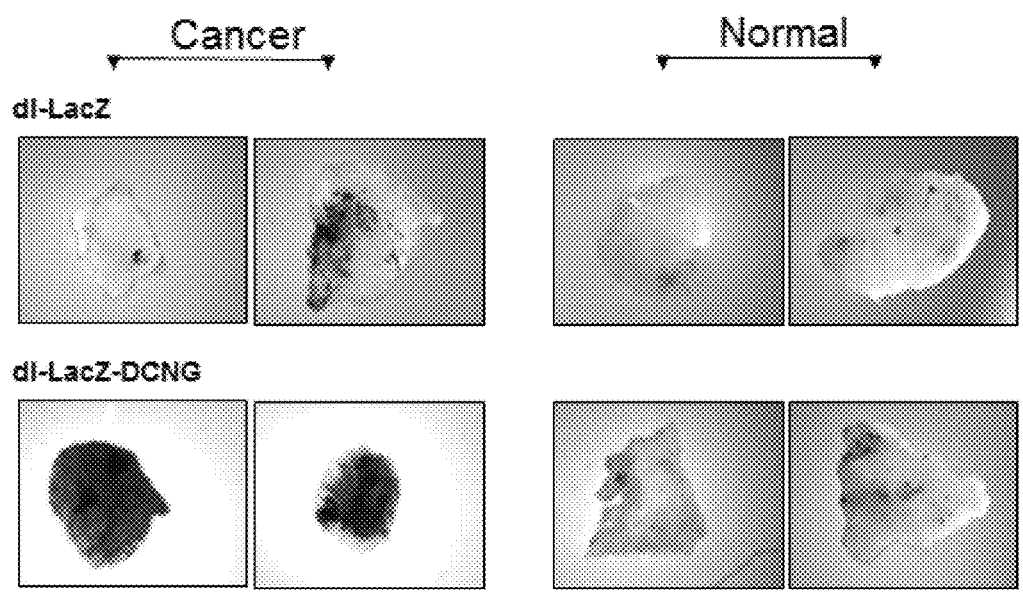
FIG. 16 represents X-gal staining results showing the tissue penetration potency and gene transduction efficiency of the decorin-expressing replication-incompetent adenovirus (dl-lacZ-DCNG) in tumor tissues and adjacent normal tissues from the patients with breast cancer.

13. Evaluation of Transduction Efficiency and Tissue Penetration Potency on Decorin-Expressing Adenovirus Using Tumor Tissues from Breast Cancer Patients To examine whether the enhanced transduction efficiency and tissue penetration potency of decorin-expressing adenoviruses as verified in Examples described above is also exhibited in primary human tumor tissues, tumor tissues and adjacent normal tissues from breast cancer patients were collected, cut into 1-2 mm diameter sections and cultured on 0.75% agarose-coated plates, followed by infecting with dl-LacZ or dl-LacZ-DCNG at $1 \times 10^8$ PFU. On day 5 after viral injection, X-gal staining was performed. The surface of tumor tissues injected with dl-LacZ-DCNG showed darker blue color compared to that injected with dl-LacZ (FIG. 16). In contrast to this, normal tissues infected with either dl-LacZ-DCNG or dl-LacZ showed little or no X-gal staining.

Figure 19B:
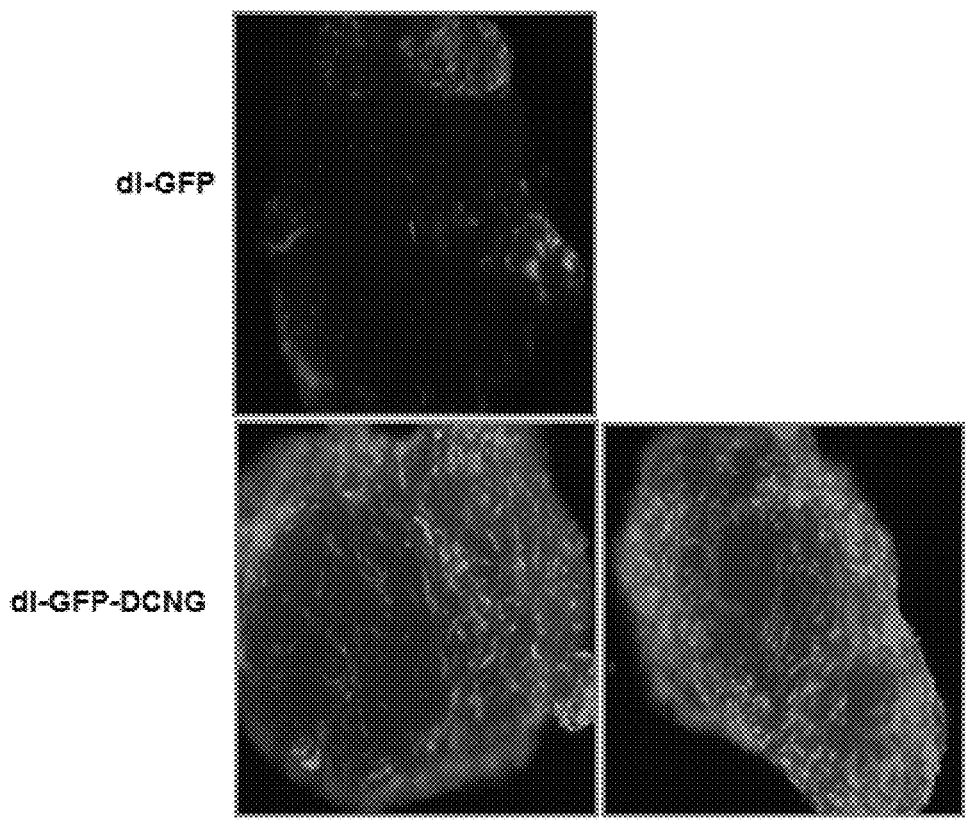
FIG. 19b is a photograph (×40) of the fluorescent microscope demonstrating the transduction efficiency and tissue penetration potency of dl-GFP or dl-GFP-DCNG in tumor tissues obtained from patients with breast cancer.

Breast tumor spheroids (<1 cm³) from breast cancer patients were plated into 12-well plates containing 5% IMDM supplemented with insulin (10 μmol) and hydrocortisone (1 μmol) and infected with dl-GFP or dl-GFP-DCNG at $1 \times 10^7$ PFU. On day 5 after viral infection, the tumor spheroids were observed under fluorescence microscope. In tumor spheroids injected with dl-GFP, GFP was limitedly expressed on the surface of tumor spheroids; however, GFP was strongly and widely expressed in most of tissues in tumor spheroids injected with dl-GFP-DCN (FIG. 19b).

Figure 17:
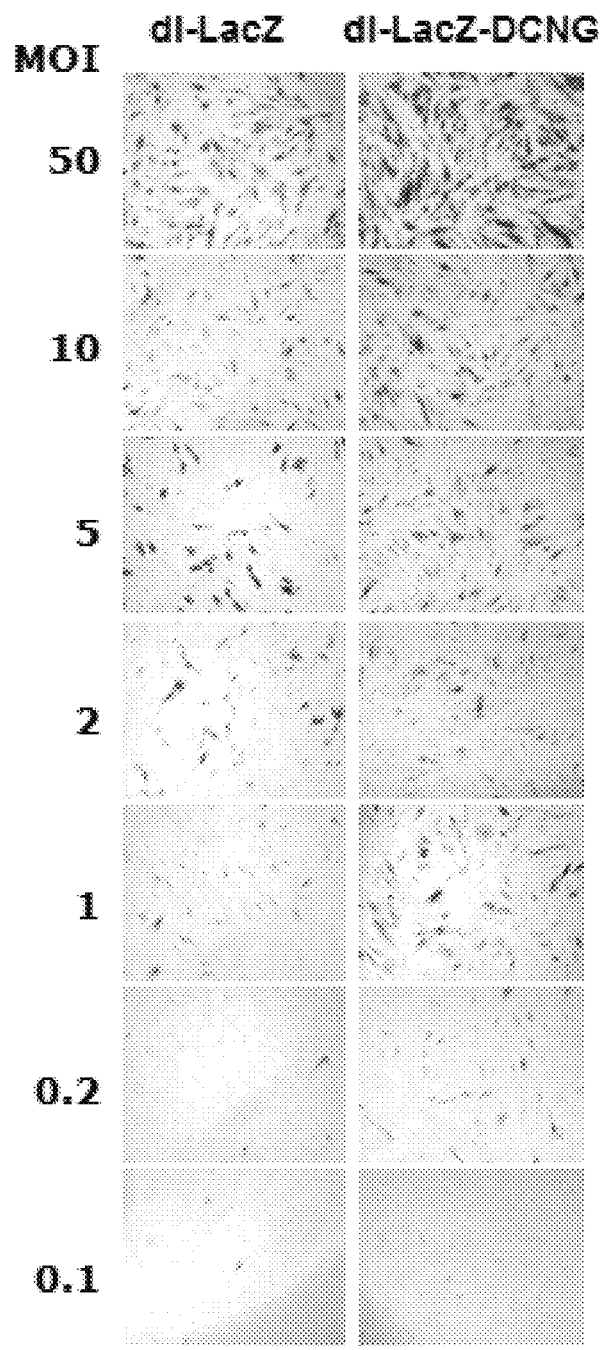
FIG. 17 represents X-gal staining results demonstrating the transduction efficiency of the decorin-expressing replication-incompetent adenovirus (dl-LacZ-DCNG) in primary keloid cells.

14. Evaluation on Transduction Efficiency of Decorin-Expressing Adenovirus on Primary Keloid Cell Keloid is one of disorders caused by the extensive formation of extracellular matrix. To assess the therapeutic efficacy of decorin-expressing adenoviruses on keloid, the primary keloid cell line from keliod patients was infected with dl-LacZ or dl-LacZ-DCNG adenovirus at an MOI of 0.1-50 and then subject to X-gal staining. It was observed that dl-LacZ-DCNG induced much stronger LacZ expression than dl-LacZ, demonstrating that the decorin expression is responsible for the significant increase in the transduction efficiency into keloid cells (FIG. 17).

15. Evaluation on Transduction Efficiency Using Keloid Spheroid Model

Figure 18:
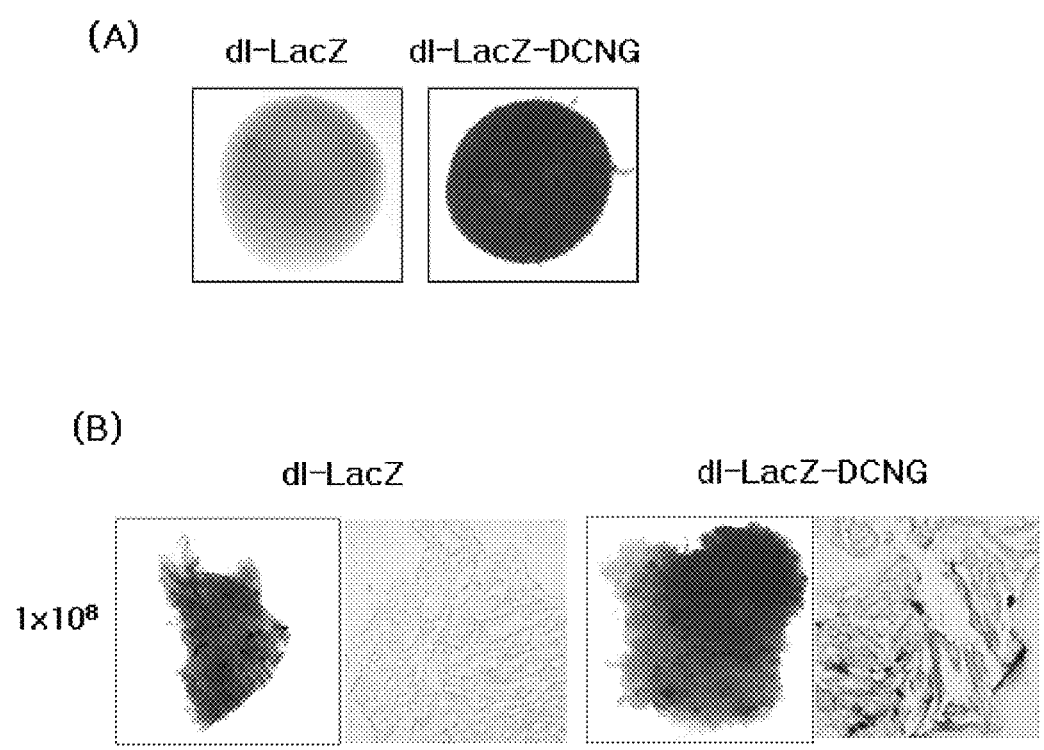
FIG. 18 is an X-gal staining photograph demonstrating the transduction efficiency of the decorin-expressing replication-incompetent adenovirus (dl-LacZ-DCNG) to keloid cell spheroid (panel A) and tissues (panel B).

To verify the improved transduction efficiency of the decorin-expressing adenovirus into keloid tissues, keloid cell spheroids prepared using primary keloid cells at passage 2 from keloid patients were infected with dl-LacZ or dl-LacZ-DCNG adenovirus at $1 \times 10^7$ PFU and subject to X-gal staining for microscopic observation. The surface of keloid cell spheroids was more intensively stained for dl-LacZ-DCNG than dl-LacZ (FIG. 18, panel A).

16. Evaluation on Spreading and Penetration Potency to Tissues from Keloid Patients To examine whether the enhanced transduction efficiency of dl-LacZ-DCNG revealed by using keloid cell spheroids is also reproducible in keloid tissues from patients, keloid tissues from patients were infected with dl-LacZ or dl-LacZ-DCNG at $1 \times 10^8$ PFU and subject to X-gal staining for microscopic observation. While dl-LacZ-treated keloid tissues showed weak LacZ expression, dl-LacZ-DCNG-treated keloid tissues were intensively X-gal stained (FIG. 18, panel B). Furthermore, in order to assess the penetration efficiency of adenoviruses into keloid tissues, the infected tissues were embedded in O.C.T. compound and snap frozen. The inner part of keloid tissues infected with dl-LacZ was far poorly stained as their surface. In marked contrast, for tissues infected with dl-LacZ-DCNG, the distribution of LacZ expression was much more extensive and was observed throughout the entire spheroid not limited to injection site (FIG. 18, panel B). These data clearly show that the transduction efficiency of the decorin-expressing adenovirus to induce the disruption of extracellular matrix is significantly enhanced in keloid tissues, demonstrating that the decorin-expressing adenovirus is a promising therapeutic agent to treat keloid disorder.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for enhancing transduction efficiency of a recombinant adenovirus expression vector into a tumor cell in a solid tumor, the method comprising:
   a. preparing a replication incompetent recombinant adenovirus expression vector comprising an adenovirus wild-type genome, the recombinant adenovirus expression vector comprising a first nucleotide sequence of interest operably linked to a first promoter and a polyadenylation sequence (promoter-nucleotide sequence of interest-poly A sequence) and a second nucleotide sequence encoding a wild type decorin operably linked to a second promoter and a polyadenylation sequence (promoter-decorin-encoding nucleotide sequence-poly A sequence), wherein the E3 region and the E1 region of the recombinant adenovirus genome sequence are deleted, wherein the promoter-nucleotide sequence of interest-poly A sequence and the promoter-decorin-encoding nucleotide sequence-poly A sequence are inserted into the deleted E3 region and E1 region, respectively, of the adenovirus genome sequence; and
   b. infecting the tumor cell with the prepared recombinant adenovirus expression vector by administering to a subject having the solid tumor the prepared recombinant adenovirus expression vector via intravenous, intraperitoneal, intramuscular, subcutaneous or transdermal route, or intratumoral injection, wherein expression of wild type decorin in the tumor cell infected with the prepared recombinant adenovirus expression vector enhances transduction efficiency of the prepared recombinant adenovirus expression vector which has not yet infected the tumor cell by binding of the expressed wild type decorin to type-I collagen fibril in an extracellular matrix of connective tissue surrounding the tumor cell.

2. The method according to claim 1, wherein the recombinant adenovirus expression vector further comprises a nucleotide sequence of interest operably linked to a promoter and a polyadenylation sequence (promoter-nucleotide sequence of interest-poly A sequence) in addition to the first nucleotide sequence inserted into adenoviral wild-type genome.

3. A method for enhancing transduction efficiency of a recombinant adenovirus expression vector into a tumor cell in a solid tumor, the method comprising:
   a. preparing an oncolytic recombinant adenovirus expression vector comprising an adenovirus wild-type genome, the recombinant adenovirus expression vector comprising a nucleotide sequence encoding a wild type decorin operably linked to a promoter and a polyadenylation sequence (promoter-decorin-encoding nucleotide sequence-poly A sequence), wherein the promoter-decorin-encoding nucleotide sequence-poly A sequence is inserted into a deleted E1B region of the adenovirus genome sequence wherein the recombinant adenovirus expression vector comprises an active E1A gene; and
   b. infecting the tumor cell with the prepared recombinant adenovirus expression vector by administering to a subject having the solid tumor the prepared recombinant adenovirus expression vector via intravenous, intraperitoneal, intramuscular, subcutaneous or transdermal route, or intratumoral injection, wherein expression of a wild type decorin in the tumor cell infected with the prepared recombinant adenovirus expression vector enhances transduction efficiency of the prepared recombinant adenovirus expression vector which has not yet infected the tumor cell by binding of the expressed a wild type decorin to type-I collagen fibril in an extracellular matrix of connective tissue surrounding the tumor cell.

4. The method according to claim 3, wherein the prepared recombinant adenovirus expression vector comprises an inactivated gene selected from the group consisting of an inactivated E1B 19 gene, an inactivated E1B 55 gene, and an inactivated E1B 19 and E1B 55 genes.

5. A method for treating a cancer of a subject having a solid tumor, the method comprising: administering to the subject a replication incompetent recombinant adenovirus expression vector via intratumoral injection, wherein the replication incompetent recombinant adenovirus expression vector comprises a first nucleotide sequence encoding an antitumor protein operably linked to a first promoter and a polyadenylation sequence (promoter-antitumor protein-encoding nucleotide sequence-poly A sequence) and a second nucleotide sequence encoding a wild type decorin operably linked to a second promoter and a polyadenylation sequence (promoter-decorin-encoding nucleotide sequence-poly A sequence); wherein the E3 region and the E1 region of the recombinant adenovirus genome sequences are deleted, wherein the promoter—an antitumor protein-poly A sequence and the promoter-decorin-encoding nucleotide sequence-poly A sequence are inserted into the deleted E3 or the deleted E1 region of the adenovirus genome sequence; wherein expression of wild type decorin in cells of the solid tumor infected with the recombinant adenovirus expression vector enhances transduction efficiency of the recombinant adenovirus expression vector which has not yet infected the tumor cells, and wherein the method is performed without exogenous addition of a protease during transduction.

6. The method according to claim 5, wherein the promoter-antitumor protein-encoding nucleotide sequence-poly A sequence is inserted into the deleted E1 region and the promoter-decorin-encoding nucleotide sequence-poly A sequence is inserted into the deleted E3 region.

7. The method according to claim 5, wherein the promoter-antitumor protein-encoding nucleotide sequence-poly A sequence is inserted into the deleted E3 region and the promoter-decorin-encoding nucleotide sequence-poly A sequence is inserted into the deleted E1 region.

8. A method for treating a cancer of a subject having a solid tumor, the method comprising: administering to the subject an oncolytic recombinant adenovirus expression vector via intratumoral injection, wherein the oncolytic recombinant adenovirus expression vector comprises a nucleotide sequence encoding a wild type decorin operably linked to a promoter and a polyadenylation sequence (promoter-decorin-encoding nucleotide sequence-poly A sequence), wherein the promoter-decorin-encoding nucleotide sequence-poly A sequence is inserted into a deleted E1B region of the adenovirus genome sequence wherein the recombinant adenovirus expression vector comprises an active E1A gene; wherein expression of wild type decorin in cells of the solid tumor infected with the recombinant adenovirus expression vector enhances transduction efficiency of the recombinant adenovirus expression vector which has not yet infected the tumor cells, and wherein the method is performed without exogenous addition of a protease during transduction.

9. The method according to claim 8, wherein the recombinant adenovirus expression vector comprises an inactivated gene selected from the group consisting of an inactivated E1B 19 gene, an inactivated E1B 55 gene, and an inactivated E1B 19 and E1B 55 genes.

* * * * *